United States Patent [19]

Seshi

[11] Patent Number: 5,521,067
[45] Date of Patent: May 28, 1996

[54] BONE MARROW CELL ADHESION MOLECULES AND PROCESS FOR DETECTING ADHERENCE BETWEEN CELL ADHESION MOLECULES AND CELLS GENERALLY

[75] Inventor: Beerelli Seshi, Fairport, N.Y.

[73] Assignee: University of Rochester, Rochester, N.Y.

[21] Appl. No.: 158,936

[22] Filed: Nov. 24, 1993

[51] Int. Cl.$^6$ .......................... G01N 33/53; G01N 33/561
[52] U.S. Cl. .......................... 435/7.24; 435/7.2; 435/7.9; 435/29; 435/961; 435/962; 436/63; 436/516
[58] Field of Search .......................... 435/7.24, 29, 7.2, 435/961, 962, 7.9; 436/63, 516

[56] References Cited

U.S. PATENT DOCUMENTS 5,270,168  12/1993  Grinnell .................................. 435/7.21

OTHER PUBLICATIONS

Seshi, B., "Cell Blotting: Techniques for Staining and Microscopical Examination of Cells Blotted on Nitrocellulose Paper," *Analytical Biochemistry*, 157:331–42 (1986).

Isberg, R. R., et al., "Cultured Mammalian Cells Attach to the Invasin Protein of Yersinia pseudotuberculosis," *Proc. Natl. Acad. Sci. USA*, 85: 6682–86 (1988.

Ferro, V., et al., "Blotting Analysis of Adhesive Proteins: An Evaluation of the Technique Using B16F10 Malignant Melanoma Cells," *Biochemical Socity Transations*, pp. 144–146 (1988).

Ward, H. D., et al. "Identification and Characterization of Taglin, a Mannose 6–Phosphate Binding Trypsin–Activated Lectin from *Giardia lamblia*," *Biochemistry*, 26:3669–75 (1987).

Wong, H. J., et al., "Cell Adhesion to Low–M$_r$ Proteins Extractable from Mineralized and Soft Connective Tissues," *Biochem. J.* 232:119–23 (1985).

Hayman, E. G., "Cell Attachment on Replicas of SDS Polyacrylamide Gels Reveals Two Adhesive Plasma Proteins," *The Journal of Cell Biology*, 95:20–23 (1982).

A. D. Campbell, et al., "Haemonectin, a Bone Marrow Adhesion Protein Specific for Cells of Granulocyte Lineage," *Nature* 329:744–46 (1987).

Miyake, Y., et al., "Requirement for VLA–4 and VLA–5 Integrins in Lymphoma Cells Binding to and Migration Beneath Stromal Cells in Culture," *The Journal of Cell Biology* 119:653–62 (1992).

Kessler, S. W., "Use of Protein A–Bearing Staphylococci for the Immunoprecipitation and Isolation of Antigens from Cells," *Methods in Enzymology*, 73:442–59 (1981).

Simmons, P. J., et al., "Vascular Cell Adhesion Molecule–1 Expressed by Bone Marrow Stromal Cells Mediates the Binding of Hematopoietic Progenitor Cells," *Blood*, 80:388–95 (1992).

DeRossi, G., et al., "Adhesion Molecule Expression on B–Cell Chronic Lymphocytic Leukemia Cells: Malignant Cell Phenotypes Define Distinct Disease Subsets," *Blood*, 81:2679–87 (1993).

Stamenkovic, I., et al., "A Lymphocyte Molecule Implicated in Lymph Node Homing Is a Member of the Cartilage Link Protein Family," *Cell*, 56:1057–62 (1989).

(List continued on next page.)

*Primary Examiner*—David Saunders
*Attorney, Agent, or Firm*—Nixon, Hargrave, Devans & Doyle

[57] ABSTRACT

The present invention relates to proteins associated with human bone marrow cell membranes for adhering hematopoietic cells to human bone marrow cell membranes. These proteins are soluble in lithium dodecyl sulfate but insoluble in 2% nonaethylene glycol octylphenol ether (e.g., 2% Triton® X-100) solution. These proteins and antibodies raised against them are useful in the treatment and diagnosis of blood disorders. The DNA molecules encoding these proteins have use in gene therapy regimes. Also disclosed is a method for detecting binding between cell adhesion membrane proteins and cells having a potential to be bound to such proteins.

8 Claims, 11 Drawing Sheets

OTHER PUBLICATIONS

Holzmann, B., et al., "Identification of a Murine Peyer's Patch-Specific Lymphocyte Homing Receptor as an Integrin Molecule with an α Chain Homologous to Human VLA-4α," *Cell*, 56:37-46 (1989).

Myers, C. L., et al., "Discriminatory Effects of Protein Kinase Inhibitors and Calcium Ionophore on Edothelial ICAM-1 Induction," *Am. J. Physiol.*, 262:C364 (1992).

A. R. deFougerolles, et al., "Characterization of ICAM-2 and Evidence for a Third Counter-Receptor for LFA-1," *J. Exp. Med.*, 174:253-67 (1991).

Hammerl, P., et al., "Antigenic Competition in the Immune Response Against Protein Mixtures: Strain-Specific Non--Immunogenicity of *Escherichia Coli* Antigens," *Molecular Immnology*, 26:313-20 (1988).

Thalhamer, J., et al. "Passive Immunization: a Method of Enhancing the Immune Response Against Antigen Mixtures," *J. of Immunological Methods*, 80:7-13 (1985).

Bevilacqua, M. P., et al., "Identification of an Inducible Endothelial-leukocyte Adhesion Molecule," *Proc. Natl. Acad. Sci. USA*, 84:9238-42 (1987).

Yutaro, S., et al., "A Novel 37-Kd Adhesive Membrane Protein from Cloned Murine Bone Marrow Stromal Cells and Cloned Murine Hematopoietic Progenitor Cells," *Blood*, 82:1436-44 (1993).

Aizawa, S., et al., "In vitro Homing of Hemopoietic Stem Cells is Mediated by a Recognition System with Galactosyl and Mannosyl Specificities," *Proc. Natl. Acad. Sci. USA*, 84:4485-89 (1987).

Tavassoli, M., et al., "Molecular Basis of the Recognition of Progenitor Cells by Marrow Stroma," *Hematopoieses*, pp. 145-55 (1990).

B. Seshi, *Biol Abstr.*, 98, Abstr. No. 1311, 1994.

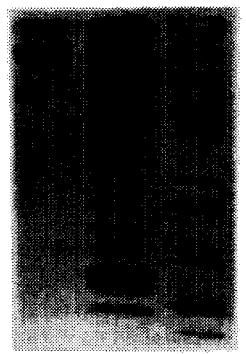
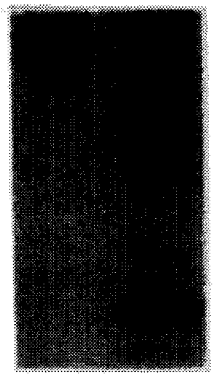
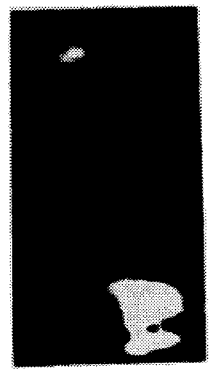
FIG.13A   FIG.13B   FIG.13C
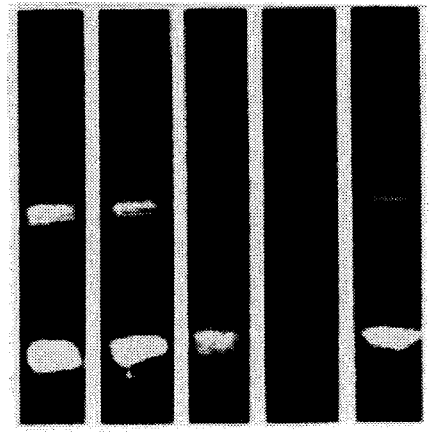
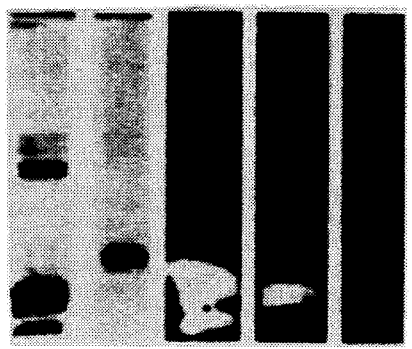
FIG.14A   FIG.14B

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:1:

Glu  Ile  Leu  Asp  Val  Pro  Ser  Thr
    1                       5

BONE MARROW CELL ADHESION MOLECULES AND PROCESS FOR DETECTING ADHERENCE BETWEEN CELL ADHESION MOLECULES AND CELLS GENERALLY

Support for this invention was provided by the National Institute of Health as a Biomedical Research Support Grant (BRGS) No. PHS S7RR05403-29.

FIELD OF THE INVENTION

The present invention relates to bone marrow cell adhesion molecules and a method for detecting adherence between cell adhesion molecules and cells.

ABBREVIATIONS USED

BSA is bovine serum albumin; CB is Coomassie Blue; CHAPS is (3-[(3-cholamidopropyl)-dimethylammonio]-1 propanesulfonate); Con A is concanavalin A; $ddH_2O$ is double distilled water; ECM is extracellular matrix; EDTA is ethylenediaminetetraacetic acid; FBS is fetal bovine serum; HMW is high molecular weight; lADS is lithium dodecyl sulfate; LMW is low molecular weight; NC is nitrocellulose; MAb is monoclonal antibody; NP-40 is nonidet P-40; PAGE is polyacrylamide gel electrophoresis; PBS(+) is phosphate-buffered saline containing calcium and magnesium; PBS-CMF is calcium and magnesium-free PBS; PHA is phytohemagglutinin; PI is propidium iodide; PVDF is polyvinylidene difluoride; rpm is revolutions per minute; RPMI 1640 is Roswell Park Memorial Institute cell culture medium; SDS is sodium dodecyl sulfate; Tris is tris-(hydroxymethyl)amino-methane; UV is ultraviolet; VCAM-1 is vascular cell adhesion molecule-1; WGA is wheat germ agglutinin.

BACKGROUND OF THE INVENTION

Cell adhesion to protein blots on nitrocellulose ("NC") following fractionation of proteins by sodium dodecyl sulfate-polyacrylamide gel electrophoresis (SDS-PAGE) was first published in 1982 (Hayman, E. G., Engvall, E., A'Hearn, E., Barnes, D., Pierschbacher, M., and Ruoslahti, E., *J. Cell Biol.* 95:20–23 (1982)). Methods for staining and detection of cells adherent to NC were described in 1986 (Seshi, B., *Anal. Biochem.* 157:331–342 (1986)). However, despite the apparent simplicity in concept, the cell blotting technique has been used only on occasion (Wong, H. J., Aubin, J. E., Wasi, S., and Sodek, J., *Biochem. J.* 232: 119–123 (1985); Ward, H. D., Lev, B. I., Kane, A. V., Keusch, G. T., and Pereira, M. E. A., *Biochemistry* 26: 8669–8675 (1987); Campbell, A. D., Long, M. W., and Wicha, M. S., *Nature* 329: 744–746 (1987); Ferro, V., D'Arrigo, C., Ogden, D., and Evans, C. W., *Biochem. Soc. Transactions* 16: 144–146 (1988); Isberg, R. R., and Leong, J. M., *Proc. Natl. Acad. Sci. USA* 85: 6682–6686 (1988)) and has not become a mainstream technique of biological investigation like the southern (Southern, E. M., *J. Mol. Biol.* 98:503–517 (1975)) and western blotting techniques, (Towbin, H. Staehelin, T., and Gordon, J., *Proc. Natl. Acad. Sci. USA* 76:4350–4354 (1979); Burnette, W. N., *Anal. Biochem.* 112:195–203 (1981)). There are two potential reasons why the technique has failed to achieve practical application. Firstly, prior to a successful cell adhesion assay on blots, cell adhesion molecules ("CAM") need to be extracted, fractionated, and blotted in a functional form; i.e., they need to withstand exposure to various detergents, as well as other steps in electrophoresis and blotting procedures, while still retaining their ability to mediate physiologically relevant adhesion function. This question has not been systematically studied in relation to the CAMs. Secondly, NC paper is not the best membrane available for protein blotting. It is fragile, not very resistant to chemicals, and difficult to handle during the cell adhesion assay. NC also does not retain protein well, thus potentially compromising sensitivity. However, practical methods for detecting cells adherent on PVDF membranes have not been described.

It has been hypothesized that normal hematopoiesis occurs as a consequence of complex interactions of hematopoietic progenitor cells ("HPC") with proteins expressed on marrow stromal cell/fibroblast membranes, as well as extracellular matrix proteins and soluble mediators secreted by these cells (Torok-Storb B., *Blood* 72:373 (1988)). Various investigators have shown that normal HPC and myeloid leukemic blast cells alike exhibit interaction and adhesion to cultured bone marrow ("BM") stromal cells/fibroblasts (Liesveld J. L., Abboud C. N., Duerst R. E., Ryan D. H., Brennan J. K., Litchman M. A., *Blood* 73: 1794 (1989); Liesveld J. L., Winslow J. M., Kempski M. C., Ryan D. H., Brennan J. K., Abboud C. N., *Exp. Hematol.* 19: 63 (1991); Gordon M. Y., Dowding C. R., Riley G. P., Goldman J. M., Greaves M. F., *Nature* 328:342 (1987)). Of special significance is the finding that HPC and leukemic blasts not only exhibit adherence to cultured marrow stromal cells/fibroblasts but actually need them to escape from apoptosis and for proliferation in culture (Manabe A., Coustan-Smith E., Behm F. G., Raimondi S. C., Campana D., *Blood* 79:2370 (1992)). Stromal cells and fibroblasts represent populations of supporting cells of the BM microenvironment. In practice, fibroblasts are grown by culturing BM in a standard culture medium containing fetal bovine serum (FBS), whereas a stromal cell layer is grown by supplementing the standard cell culture medium with horse serum and hydrocortisone (Dexter-type cultures). Stromal cells are morphologically heterogeneous and exhibit adipocyte differentiation whereas fibroblasts do not show such features. Stromal cells play an important supportive role in myelopoiesis whereas fibroblasts are required for in vitro lymphopoiesis. Therefore, it is of great interest to investigate interactions of HPC and their leukemic counterparts with the stromal cells as well as fibroblasts.

In vitro proliferation of normal human and murine lymphoid progenitors requires adhesion to BM fibroblasts mediated by the integrin adhesion protein VLA-4 ("very late antigen-4 or α4/β1 integrin or CDw49d/CD29") (Kincade P. W., *Sem. Immunol.* 3:379 (1991)). The role of known adhesion molecules in myelopoiesis and proliferation of leukemic cells is less clear. Tavassoli et al have shown that a 110 Kd membrane protein on murine myeloid HPC mediates their adhesion to stromal cells and, in fact, inhibition of this adhesion blocks growth of the HPC (Tavassoli M., Aizawa S., Matsuoka T., Hardy C., in Golde D. W. (ed), *Hematopoiesis,* New York, N.Y., Alan R. Liss, Inc. (1990), p 145; Aizawa S., Tavassoli M., *Proc. Natl. Acad. Sci. USA* 84:4485 (1987)). A corresponding ligand protein of 37 Kd has recently been identified on murine BM stromal cells (Shiota Y., Wilson J. G., Harjes K., Zanjani E. D., Tavassoli M., *Blood* 82: 1436 (1993)). Therefore, adhesion to marrow stromal cells appears to play a pivotal role at least in normal hematopoiesis. However, no human counterpart involved in homing of HPC to marrow has been identified. Some reports suggest that VLA-4 and its ligand VCAM-1 (vascular cell adhesion molecule-1) are partially responsible for adherence between myeloid HPC and BM stromal cells (Miyake K., Hasunuma Y., Yagita H., Kimoto M., *J. Cell Biol.* 119: 653 (1992); Simmons P. J., Masinovsky B., Longenecker B. M., Berenson R., Torok-Storb B., Gallatin W. M., *Blood* 80: 388 (1992)). Based on failure to abrogate complete binding between HPC and BM stroma using anti-VCAM-1 antibodies alone or in combination with EILDVPST (Seq. I.D. No. 1) peptide, the latter investigators concluded a probable role for other unknown CAMs in mediating adhesion between HPC and BM stroma (Simmons P. J., Masinovsky B., Longenecker B. M., Berenson R., Torok-Storb B., Gallatin W. M., *Blood* 80:388 (1992)).

The conventional method for investigating unknown CAMs is indirect and requires generating MAbs to whole cells or plasma membrane components and then using the MAbs to block cell-cell adhesion (Bevilacqua M. P., Pober J. S., Mendrick D. L., Cotran R. S., Gimbrone Jr M. A., *Proc. Natl. Acad. Sci. USA* 84: 9238 (1987)). However, use of whole cells or crude mixtures of proteins as immunogens may present the problem of antigenic competition, the situation in which one antigen can suppress the response to another and consequently antibodies may not form for antigens of interest (Thaihamer J., Freund J., *J. Immunol. Methods* 80: 7 (1985); Hammerl P., Weger R., Thaihamer J., *Mol. Immunol.* 25: 313 (1988)). Even if MAbs are developed, they may not have the functional blocking activity. Even if they have the blocking activity, they may not identify the molecule of interest at the biochemical level for the following reason. The conventional technique that has been used for biochemical detection of some of the known CAMs such as ELAM-1 (endothelial-leukocyte adhesion molecule-1) (Bevilacqua M. P., Pober J. S., Mendrick D. L., Cotran R. S., Gimbrone Jr. M. A., *Proc. Natl. Acad. Sci. USA* 84: 9238 (1987)); CD54 (Myers C. L., Desai S. N., Schembri-King J., Letts G. L., Wallace R. W., *Am. J. Physiol.* 262:C365 (1992)); ICAM-2 (intercelluglar adhesion molecule-2) (de Fougerolles A. R., Stacker S. A., Schwarting R., Springer T. A., *J. Exp. Med.* 174:253 (1991)); VCAM-1 (Simmons P. J., Masinovsky B., Longenecker B. M., Berenson R., Torok-Storb B., Gallatin W. M., *Blood* 80: 388 (1992)); VLA-4 (Holzmann B. , Mcintyre B. W., Weissman I. L., *Cell* 56:37 (1989)); CD44 (Stamenkovic I., Amiot M., Pesando J. M., Seed B., *Cell* 56:1057 (1989)); and CD61 (Rossi G. D., Zarcone D., Mauro F., Cerruti G., Tenca C., Puccetti A., Mandelli F., Grossi C. E., *Blood* 81: 2679 (1993)) consists of, a) Labeling of cell surface proteins, b) Extraction of the labeled molecules by NP-40 (nonidet P-40) or Triton® X-100 ranging in concentration from 0.5% to 2%, c) Immunoprecipatation of the solubilized molecules using an appropriate MAb (Kessler S. W., in Langone J. J., Vunakis H. V. (eds), "Methods in Enzymology," vol. 73, New York, N.Y., Academic Press (1981) p. 442), and d) SDS-PAGE (sodium dodecyl sulfate-polyacrylamide gel electrophoresis) followed by autoradiography or western blotting if the cells had been biotin-labeled instead of radiolabeled. While most known CAMs are extractable by Triton® X-100 or NP-40 and, therefore, can be detected by the standard immunoprecipatation technique, it is apparent that the standard technique would not identify new CAMs if they are not solubilized by Triton® X-100 or NP-40.

SUMMARY OF THE INVENTION

The present invention relates to isolated proteins associated with human bone marrow cell membranes for adhering hematopoietic cells to the human bone marrow cell membranes. These proteins are soluble in lithium dodecyl sulfate but not in a 2% nonaethylene glycol octylphenol ether (i.e., Triton® X-100, which is available from Bio-Rad, Hercules, Calif.) solution.

Each of the isolated proteins can be produced by a corresponding DNA molecule encoding for it. That DNA molecule can be inserted as-a heterologous DNA molecule in an expression vector forming a recombinant DNA expression system for producing the encoded protein. Likewise, the DNA molecule, usually inserted in an expression vector to form a recombinant DNA expression system, can be incorporated in a cell to achieve this objective.

Each of the isolated proteins can be used to raise a corresponding antibody or a binding portion thereof.

The proteins, the antibodies or binding portions thereof, and DNA molecules of the present invention may be used alone or combined with a pharmaceutically-acceptable carrier to treat humans with blood disorders. The proteins and antibodies or binding portions thereof can be utilized to treat patients with leukemia or lymphoma by preventing leukemia or lymphoma cells from binding to and being nourished by bone marrow supporting structure. The DNA molecule of the present invention is utilized to cure genetic deficiencies in a patients ability to produce these encoded proteins. Such deficiencies can be overcome by gene therapy.

The proteins of the present invention can be used to detect blood-disorders in humans by obtaining bone marrow cells from patients with blood disorders. The cells are then cultured in a monolayer and lysed to form a cell lysate. The lysate is centrifuged at low speed, and the pellet of cell nuclear material is discarded. The supernatant containing cell membranes is then centrifuged at high speed to form a membrane pellet. That pellet is then solubilized in lithium dodecyl sulfate to form a solution. The solution is subjected to polyacrylamide gel electrophoresis to separate the cell adhesion molecule proteins by size and charge within the gel. The gel is then contacted with a blotting material to transfer the separated cell adhesion molecule proteins to the blotting material. Hematopoietic cells are then applied to the blotting material where they bind to the blotted cell adhesion molecule proteins. The blotting material is stained to detect the separated cell adhesion molecule proteins by reaction with the added hemoatopoitic cells, and the stained blotting material is compared with a stained blotting material similarly obtained from healthy bone marrow cells to determine whether there are any differences between their cell adhesion molecule proteins.

Human blood disorders may also be detected by antibodies or binding portions thereof raised against the cell adhesion molecule proteins of the present invention. Any reaction between a sample of bone marrow or bone marrow cell adhesion molecule proteins and the antibody or binding portion thereof is detected using an assay system which indicates the presence of the protein of the present invention in a particular sample.

The DNA molecule of the present invention can also be used for diagnostic purposes. For example, the DNA sequence of stromal cells in patients with blood disorders can be compared to those cells in healthy individuals for indication of genetic abnormality.

In another aspect of the present invention, a method for detecting binding between cell adhesion molecule proteins and cells having the potential for such binding is also disclosed. This process involves solubilizing a solid pellet containing cell adhesion molecule proteins with lithium dodecyl sulfate to form a solution. The solution is then subjected polyacrylamide gel electrophoresis to form a gel containing the cell adhesion molecules which are separated by size and charge. The gel is then contacted with a blotting material to transfer separated cell adhesion molecule proteins to the blotting material. Cells having a potential to bind to the blotted cell adhesion molecule proteins are then applied to the blotting material. In some instances, the blotting material is then stained to detect the separated cell adhesion molecule proteins by reaction with the added cells, and the stained blotting material is examined for indications of such binding between cell adhesion molecule proteins and cells.

The isolation of the bone marrow cell adhesion molecule proteins of the present invention constitutes a significant advance in the treatment and detection of blood disorders. It provides the basis for treating a number of blood disorders by treatment with cell adhesion molecule proteins or with antibodies or binding portions thereof raised by these proteins or gene therapy with the DNA molecule encoding for these proteins.

In diagnostic applications, the antibodies and binding portions thereof raised by the protein of the present invention permit rapid determination of whether a particular individual has a particular blood disorder. Knowledge of the cell adhesion molecule proteins of the present invention found in healthy bone marrow cells provides a basis for comparing bone marrow cells in a test sample to determine whether the patient from whom the latter cells are taken has a blood disorder.

The method of the present invention for isolating cell adhesion molecule proteins in general is also a significant advance, because it enables cell adhesion molecule proteins for virtually any cell to be isolated and analyzed. This is significant, because it provides a simple and powerful tool to identify cell adhesion molecule proteins involved in cell-to-cell interactions generally, beginning with egg-sperm interactions, embryonic cell migrations during embryogenesis or organogenesis, homing of lymphocytes to particular lymphoid tissues, spread of cancer cells to different organs, and interactions between different infection agents and their host cells.

BRIEF DESCRIPTION OF THE DRAWINGS

In FIG. 3A, "Native" PAGE gel setup was loaded with samples containing decreasing amounts of a nonionic detergent, Triton® X-100 (2%, 1%, 0.5%, 0.25% and 0.12.5%) in lanes 1–5, and decreasing amounts of a zwitterionic detergent, CHAPS (2%, 1%, 0.5%, 0.25% and 0.125%) in lanes 6–10. All samples contained 17.5 µg of albumin per lane. No LDS was present either in any sample, running buffer or gel. Following electrophoresis, protein bands were blotted onto PVDF. PVDF membrane, while drying, was monitored for chalky white material representing detergents. Only protein bands transferred to PVDF; there was no evidence of transfer of detergents to PVDF. Triton® X-100 and CHAPS, due to lack of charge, probably did not enter the gel and, therefore, would not be expected to be seen on PVDF. In FIG. 3B, LDS-PAGE gel was setup with samples in all lanes containing constant amount of LDS (0.29%) and albumin (17.5 ug). In addition, samples in lanes 1–5 contained decreasing amounts of Triton®X-100 (2%, 1%, 0.5%, 0.25% and 0.125%), and samples in lanes 6–10 contained decreasing amounts of LDS (2%, 1%, 0.5%, 0.25% and 0.125%). LDS-PAGE and subsequent blotting were performed by standard methods as described. PVDF membrane was photographed while in the process of drying when chalky white bands representing detergents appeared. Note that mixed micelles of Triton® X-100/LDS (lanes 1–5) migrated to the buffer front and transferred to PVDF and that the size of detergent bands correlates with the amount of Triton® X-100. The detergent bands were not seen in completely wet or completely dry PVDF blot. On the other hand, in lanes 6–10 containing LDS alone, no detergent bands were seen on PVDF at any time. As mentioned earlier, dot blotting of LDS solution alone and containing no Triton® X-100 produces chalky white spots, suggesting that LDS bands did not transfer to PVDF. Since LDS has a high binding affinity to polyacrylamide under cold conditions (Kubo, K. and Takagi, T., *J. Biochem.* 99:1545–1548 (1986), which is hereby incorporated by reference), only proteins were transferred to PVDF leaving LDS behind in gel and thus proteins on PVDF blot are "cleared" of LDS. In FIG. 3C, LDS-PAGE gel was setup with samples in lanes 1–5 containing a constant amount of Triton® X-100 (0.5%) and albumin (8.7 µg) and decreasing amounts of LDS (2%, 1%, 0.5%, 0.25% and 0.125%); and samples in lanes 6–10 contained a constant amount of Triton® X-100 (0.25% instead of 0.5%) and albumin (8.7 µg) and decreasing amounts of LDS (2%, 1%, 0.5%, 0.25% and 0.125%). Following electrophoresis, protein bands were blotted onto PVDF by standard methods. As above, the PVDF membrane was photographed while in the process of drying when chalky white bands representing detergents appeared. Note the size of detergent bands approximately correlating with the amount of LDS, especially at higher concentrations. Taken together with results above, these findings indicate that the presence of Triton® X-100 along with LDS in samples inhibited binding of LDS to polyacrylamide and facilitated migration to the buffer front and transfer to PVDF.

FIG. 4A shows Coomassie Blue staining of PHA in gel. Note that the HMW bands correspond to multimeric complexes and that the LMW bands correspond to monomeric units. FIG. 4B shows Coomassie Blue staining of a PHA protein blot on a PVDF membrane. FIG. 4C shows PI staining of KG1a cells adherent to PHA on PVDF, and viewed under a long wave UV light. FIG. 4D shows Hematoxylin (sequential Stain A and Stain B) staining of KG1a cells adherent to PHA on PVDF. Notably, cells exhibit adhesion to only HMW bands representing multimers of PHA, especially evident at lower concentrations of PHA. Also note that there are distinct cell bands even if corresponding protein bands are not obvious, demonstrating the extreme sensitivity of the cell blotting assay. This Figure further demonstrates that both PI stain and hematoxylin stain provide comparable and independent cell detection methods. Minor differences observed may not necessarily be due to differences in staining methods.

FIG. 5A shows Coomassie Blue staining of WGA in gel. Note that HMW bands correspond to multimeric complexes and that LMW bands correspond to monomeric units. FIG. 5B shows Coomassie Blue staining of WGA protein blot on a PVDF membrane showing minimal amounts of WGA transferred. FIG. 5C shows PI staining of KG1a cells adherent to WGA on PVDF viewed under a long wave UV light. Note significant cell binding in areas on the blot corresponding to HMW complexes of WGA in a concentration-dependent manner even though protein bands are faint. No cell binding is seen in areas corresponding to monomeric units. FIG. 5D is performed in parallel with the blot in FIG. 5C with one exception. Prior to the cell adhesion assay, while the blot in FIG. 5C received 1% BSA/PBS(+), the blot in FIG. 5D was incubated in 10 ml of 0.5M N-acetyl D-glucosamine in 1% BSA/PBS(+) for 1 hour at room temperature to block sugar binding sites of WGA. Following this blocking step, inhibitor solution was removed and the adhesion assay was performed at room temperature as usual. Note the partial blocking of binding of KG1a cells to WGA by N-acetyl D-glucosamine, suggesting the specificity of cell binding.

FIG. 6A shows Coomassie Blue staining of the protein blot on PVDF membrane. FIG. 6B shows PI staining of KG1a cells adherent to protein blot on PVDF, and viewed under a long wave UV light. Note that cells bind to HMW multimeric complexes as well as LMW fragments of Con A, and two relatively HMW bands of ECM. It may also be mentioned that cell adhesion to Con A and ECM did not appear to be as strong as cell adhesion to PHA and WGA since cell binding to Con A and ECM may be lost if the assay chamber is rocked in addition to swirled during the washing procedure, underscoring the importance of the variables involved.

FIG. 7A shows Coomassie Blue staining of the VCAM-1 protein in gel. Shown on the side are (Bio-Rad) broad range molecular weight markers (a mixture of nine proteins ranging from 200,000–6,500 daltons). Although the marker proteins appear to be resolved well and evenly distributed from top to bottom of the lane, there are clearly more than nine bands some of which most likely represent molecular complexes. Accordingly, accurate estimation of molecular weights may not be possible by this gel system. FIG. 7B shows Coomassie Blue staining of the VCAM-1 protein blot on PVDF membrane. VCAM-1 was transferred from the gel completely following blotting. Two satellite bands are observed when larger concentrations of VCAM-1 are loaded, possibly representing formation of molecular complexes or a minor fraction of protein degradation products. FIG. 7C shows PI staining of NALM-6 cells adherent to VCAM-1 on PVDF, and viewed under a long wave UV light. Note that VCAM-1 as low as 0.3 µg has produced a discernible cell band.

FIG. 8A shows a thick carpet of KG1a cells at the top and a clean background at the bottom (original magnification 100×), and FIG. 8B shows KG1a cells at a higher magnification (original magnification 200×), verifying that the PI-positive bands are due to adherent cells rather than nonspecific staining.

FIG. 9A shows a thick carpet of cells on the left side and a clean background on the right side (original magnification 100×). FIG. 9B shows the same cells, but viewed at a higher magnification (200×). While Stain A alone was quite adequate for macroscopic visualization of the cell bands, the individual cells did not appear to be uniformly stained. A combined hematoxylin stain (Stain A followed by Stain B) was needed for satisfactory visualization of individual cells under microscope.

FIG. 11A shows Coomassie Blue staining of the gel. FIG. 11B shows Coomassie Blue staining of the protein blot on a polyvinylidene difluoride membrane. FIG. 11C shows propidium iodide staining of NALM-6 cells adherent to protein blot on polyvinylidene difluoride, and viewed under a long wave UV light. FIG. 11D shows propidium iodide staining of KG1a cells adherent to a protein blot on polyvinylidene difluoride, and viewed under a long wave UV light. The thick cell band in both (FIG. 11C, lane 3) and (FIG. 11D, lane 3) actually represents three overlapping bands.

FIG. 12A shows the immunoperoxidase staining using a monoclonal antibody to VCAM-1. Samples are as described under FIG. 11. Note that VCAM-1 is exclusively present in Triton® extracts (lanes 1 and 2) but not in lithium dodecyl sulfate extract (lane 3) or urea extract (lane 4). FIG. 12B shows immunoperoxidase staining using a monoclonal antibody to CD44. Samples are as described under FIG. 11. Note that CD44 is predominantly solubilized by Triton® X-100 (lanes 1 and 2), and the trace amount of CD44 not solubilized by Triton® X-100 is extracted by lithium dodecyl sulfate and seen in lane 3. The diffuse band pattern of CD44 is also noteworthy and is consistent with its molecular heterogeneity. FIG. 12C shows immunoperoxidase staining using a monoclonal antibody to CD54 (ICAM-1). Samples are slightly different from those under FIG. 12A and FIG. 12B and are as follows: lane 1, whole cell lysate of K562 as a positive control for CD54 prepared using 0.5% Triton® X-100; lane 2, bone marrow stromal cell membrane proteins extracted by 2% Triton® X-100 (lipid rich material floating at top of supernatant); lane 3, membrane proteins extracted as in lane 2 but representing the clear portion of supernatant; lane 4, membrane proteins extracted by 0.575% lithium dodecyl sulfate; lane 5, membrane proteins extracted by 8M urea/25 mM dithiothreitol/2% (3-[(3-cholamido propyl)-dimethylammonio]-1 polysulfoxide). Note that CD54 band is strictly present in Triton® extracts and not in LDS or urea extracts and that its band position is identical to that of positive control. Trace positivity with a bone marrow cell adhesion molecule in a lithium dodecyl sulfate extract lane represents crossreactivity and may signify some relationship to the immunoglobulin super family.

FIGS. 13A–C show cell adhesion to purified protein of a known cell adhesion molecule (ie, VCAM-1) separated by lithium dodecyl sulfate-polyacrylamide gel electrophoresis using a 4–12% discontinuous gradient gel, and blotted onto polyvinylidene difluoride membrane. Samples were as follows: Lane 1, rs VCAM-1 (5 ug); and lane 2, bone marrow stromal cell membrane proteins extracted by 0.575% lithium dodecyl sulfate. Final samples contained 0.2875% lithium dodecyl sulfate and 10% glycerol in 125 mM Tris-HCl, pH 6.8, and were loaded as 35 ul/lane. FIG. 13A shows Coomassie Blue staining of the gel. Shown on the side are (Bio-Rad) broad range molecular weight markers (a mixture nine proteins ranging from 200 Kd-6.5 Kd). Although the marker proteins appear to be resolved well and evenly distributed from top to bottom of the lane, there are clearly more than nine bands some of which most likely representing molecular complexes. Consequently, accurate determination of molecular weights may not be possible by this gel system. FIG. 13B shows Coomassie Blue staining of a protein blot on polyvinylidene difluoride membrane. FIG. 13C shows propidium iodide staining of Ramos cells adherent to protein bands on polyvinylidene difluoride, and viewed under a long wave UV light. This demonstrates that the assay conditions preserve cell adhesion properties of a known cell adhesion molecule and that the bone marrow cell adhesion molecules reported here are different from VCAM-1.

FIGS. 14A–B show adhesion of different hematopoietic cells to different subsets of bone marrow stromal cell cell adhesion molecules solubilized by lithium dodecyl sulfate. FIG. 14A shows cell adhesion was assayed at 4° C. The target cells are as follows: Lane 1, NALM-6 cells; lane 2, KG1a cells; lane 3, K562 cells; lane 4, WIL-2 cells; and lane 5, HS-Sultan. Cell bands in all lanes were developed by propidium iodide stain. FIG. 14B shows cell adhesion was assayed at 37° C. The target cells are as follows: Lane 1, KG1a cells; lane 2, HS-Sultan; lane 3, Ramos; lane 4, JY B lymphoblastoid cells; and lane 5, T-lymphoblasts. Cell bands in lanes 1–2 were developed by hematoxylin stain, whereas cell bands in lanes 3–5 were developed by propidium iodide stain. It appears that progenitor cells like NALM-6 and KG1a bind to the greatest number of protein bands; on the other hand, more mature cell types such as WIL-2 and JY B lymphoblastoid cells bind to a smaller number of protein bands that are common to all cell types.

FIG. 15A shows a thick carpet of KG1a cells on the left side and a clean background on the right side (original magnification 100×), and FIG. 15B shows NALM-6 cells (original magnification 200×), verifying that the propidium iodide-positive bands are due to adherent cells rather than nonspecific staining.

FIG. 16A is a correlation between the low-power microscopic view of a cell band, cell blot, and protein blot. The top left shows Coomassie Blue staining of the protein blot on a polyvinylidene difluoride membrane, representing a replica of the lithium dodecyl sulfate-extracted proteins, while the top right reveals hematoxylin staining of myeloid progenitor (KG1a) cells adherent to protein bands on a polyvinylidene difluoride membrane. Note that some proteins are more adhesive than others as can be judged by some protein bands appearing weak on protein blot and strong on cell blot and vice versa. On the bottom, a low-power microscopic view of a band of cells confirms a positive band as due to cell binding (original magnification ×). FIG. 16B shows KG1a cells viewed at a higher magnification (200×). Note that some cells appear round and densely stained whereas most other cells appear flat and spread out.

DETAILED DESCRIPTION OF THE INVENTION

Figure 1:
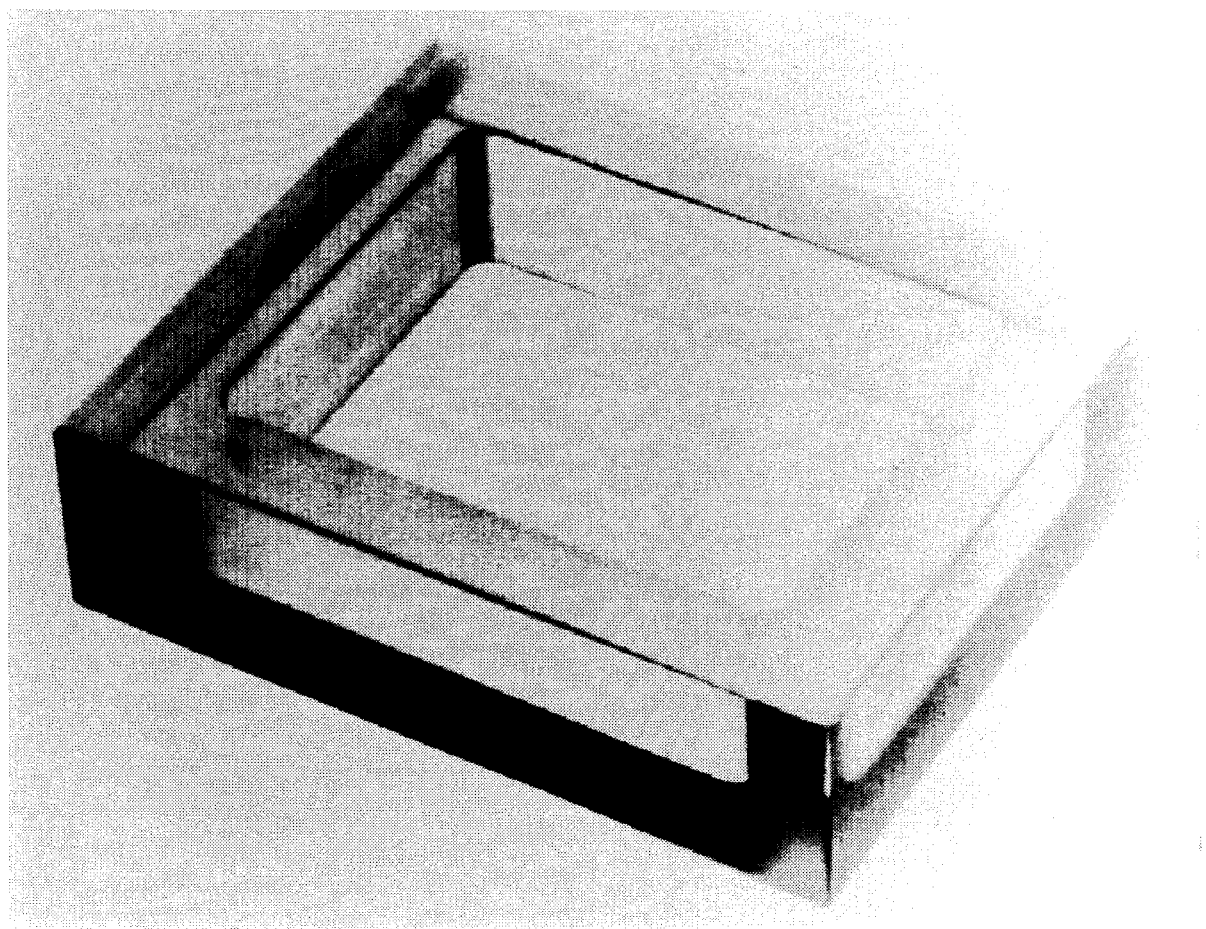
FIG. 1 is a photograph of cell-adhesion assay chamber.

The present invention relates to an isolated protein associated with human bone marrow cells for adhering hematopoietic cells to the human bone marrow cell membranes. The protein is soluble in lithium dodecyl sulfate but insoluble in 2% nonaethylene glycol octylphenol ether (i.e., Triton®

X-100, available from Bio-Rad, Hercules, Calif.) solution.

Hematopoietic cells are blood or blood forming cells, including red blood cells, white blood cells (e.g., granulocytes, lymphocytes), and platelets. Bone marrow cells are bone marrow supporting cells, such as stromal cells, fibroblasts, fat cells, endothellial cells, osteoblasts, osteoclasts, and the above hematopoietic cells.

As indicated in the examples infra, nine cell adhesion molecule proteins have been isolated from human bone marrow. All of these bind to KG1a myeloid progenitor cells (ATCC Accession No. CCL 246.1) at 37° C. or 4° C. or both. In addition, it has been found that various of these proteins also bind to the following other human leukemia or lymphoma cell lines: NALM-6 B-lymphoid progenitor, JY B-lymphoblastoid, Ramos Burkitt's B-lymphoid (ATCC Accession No. CRL 1596), HS-Sultan plasmacytoma (ATCC Accession No. CRL 1484), K 562 erythroleukemia (ATCC Accession No. CCL 243), and WIL-2 mature B-lymphoid human leukemic cells (ATCC Accession No. CRL 8155). Four of these molecules have a low molecular weight of 10 to 20 kilodaltons. One molecule has a molecular weight of 20–30 kilodaltons. Two other molecules have a molecular weight of 45 to 65 kilodaltons. The other two have a higher molecular weight of 65 to 75 kilodaltons. Table 1 sets forth the approximate molecular weight of each of these proteins as well as the particular cell lines to which they bind.

fraction containing the protein of the present invention is subjected to gel filtration in an appropriately sized dextran or polyacrylamide gel to separate the proteins. If necessary, the protein fraction may be further purified by HPLC.

From the isolated proteins described above, corresponding DNA molecules encoding those proteins can be prepared by conventional techniques. More particularly, the amino acid sequences of the cell adhesion molecule proteins can be sequenced and cDNAs can be made from mRNAs of bone marrow prepared from the cell adhesion molecule proteins. Based on the amino acid sequence data, degenerate oligonucleotide primers can be constructed and probes can be generated by amplifying the segments of cDNAs through a polymerase chain reaction (PCR). Using these short cDNA sequences as probes, full-length cDNAs can be isolated and the genomic structure and organization can be studied.

The DNA molecule encoding a protein associated with human bone marrow cell membranes for adhering hematopoietic cells to bone marrow cell membranes can be used to prepare such proteins by conventional recombinant DNA technology. Generally, this involves inserting the DNA molecule into an expression system to which the DNA molecule is heterologous (i.e. not normally present). The heterologous DNA molecule is inserted into the expression system or vector in proper orientation and correct reading frame. The vector contains the necessary elements for the transcription and translation of the inserted protein-coding sequences.

TABLE 1

|  | Protein No. | | | | | | | | |
| --- | --- | --- | --- | --- | --- | --- | --- | --- | --- |
|  | 1 | 2 | 3 | 4 | 5 | 6 | 7 | 8 | 9 |
| Approximate Molecular Weight (in kilodaltons) | 65–75 | 65–75 | 45–65 | 45–65 | 20–30 | 10–20 | 10–20 | 10–20 | 10–20 |
| KG1a myeloid progenitor (ATCC Accession No. CCL 246.1) | ✓ | ✓ | ✓ | ✓ | ✓ | ✓ | ✓ | ✓ | ✓ |
| NALM-6 B-lymphoid progenitor |  |  | ✓ | ✓ | ✓ | ✓ | ✓ | ✓ |  |
| JY B-lymphoblastoid |  |  |  |  |  |  | ✓ | ✓ |  |
| Ramos Burkitt's B-lymphoid (ATCC Accession No. CRL 1596) |  |  |  |  | ✓ | ✓ | ✓ | ✓ | ✓ |
| HS-Sultan plasmacytoma (ATCC Accession No. CRL 1484) |  | ✓ | ✓ |  |  | ✓ | ✓ |  |  |
| K 562 erythroleukemia (ATCC Accession No. CCL 243) |  |  |  |  |  | ✓ | ✓ | ✓ |  |
| WIL-2 mature B-lymphoid human leukemic cells (ATCC Accession No. CRL 8155) |  |  |  |  |  |  |  | ✓ |  |
| T-lymphoblasts |  |  |  |  |  |  |  |  |  |

✓ indicates binding

The protein of the present invention is preferably produced in purified form by conventional techniques. Typically, the protein of the present invention is secreted into the growth medium of recombinant *E. coli*. To isolate the protein, the *E. coli* host cell carrying a recombinant plasmid is propagated, homogenized, and the homogenate is centrifuged to remove bacterial debris. The supernantant is then subjected to sequential ammonium sulfate precipitation. The U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK ± or KS ± (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system, and, further, procaryotic promotors are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in *E. coli*, its bacteriophages, or plasmids, promotors such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding a protein associated with human bone marrow cell membranes for adhering hematopoietic cells to human bone marrow cell membranes has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

In view of the present invention's determination of the proteins constituting bone marrow cell adhesion molecules, a wide array of therapeutic and/or prophylactic agents and diagnostic procedures for various blood disorders can be developed.

While bone marrow cell adhesion molecule proteins provide the anchorage for leukemia cells to settle in bone marrow, other local growth factors are needed for them to grow and spread. Disrupting tile anchorage or homing environment causes leukemia cells to be deprived of necessary growth factors and, subsequently, to die. By injecting purified cell adhesion molecule proteins into the blood, the circulating bone marrow cell adhesion molecule proteins will compete with cell adhesion molecule proteins present on bone marrow stromal cells for leukemia cells. As a result, leukemia cells will be dislodged from bone marrow cell membranes and perish. The protein can be administered alone or in combination with a pharmaceutically acceptable carrier.

It is also possible to treat individuals having leukemia with an effective amount of an antibody or binding portion thereof against the protein of the present invention to block access by leukemia cells to bone marrow cell adhesion molecule proteins on the surface of stromal cells. Such antibodies or binding portions thereof are administered alone or in combination with a pharmaceutically-acceptable carrier to effect treatment of individuals with leukemia. The antibodies or binding portions thereof bind to the surfaces of bone marrow cells (i.e., stromal or fibroblast cells) which prevents leukemia cells from binding to such sites. This prevents the spread of leukemia, because leukemic cells will be deprived of growth factors needed for survival.

Antibodies suitable for use in treating leukemia can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest (i.e. the protein or peptide of the present invention) either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. The virus is carried in appropriate solutions or adjuvants. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.* 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 μl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbitol 150 mg/Kg IV. This and other procedures for raising polyclonal antibodies are disclosed in E. Harlow, et. al., editors, *Antibodies: A Laboratory Manual* (1988), which is hereby incorporated by reference.

The DNA molecules encoding proteins of the present invention are also useful in treating humans with blood disorders by use of gene therapy regimes. Such treatment may be useful for a number of blood disorders as follows. Aplastic anemias, such as Fanconi's anemia and dyskeratosis congentia, are diseases which involve bone marrow failure causing anemia which is associated with other developmental disorders. Other disorders are single-lineage bone marrow failures, including red cell failures, white cell failures, and platelet failures. Red cell failures include congenital pure red cell aplasia (i.e., Diamond-Blackfan Syndrome) and congenital dyserythropoietic anemia. White cell failures include reticular dysgenesis, Kostmann's Syndrome, and congenital benign neutropenia. Reticular dysgenesis involves a total failure of all white cell types including tymphocytes and granulocytes. Kostmann's Syndrome involves the failure of neutrophils to develop selectively, while other cell types (e.g., eosinophils,. basophils, monocytes, and lymphocytes) develop normally. Congenital benign neutropenia shows active marrow but an absence of granulocytes and some of their precursors, usually in children.

One important aspect of the present invention is that of the nine bone marrow cell adhesion molecule proteins, some bind to all lineages of hematopoietic cells, while others are restricted to particular lineages or particular stages of development of hematopoietic cells (see Table 1). The absence of lineage-specific bone marrow cell adhesion molecules would explain the etiology of some of these disorders. In addition, a deficiency of bone marrow cell adhesion molecules showing binding to multiple hematopoietic cell types would explain the etiology of bone marrow failures involving different lineages. The genes encoding for the proteins of the present invention could be administered to individuals having blood disorders characterized by an absence of the corresponding protein.

Current treatments for blood disorders have centered around colony stimulating factors ("CSF"). Such regimes have had mixed levels of success. The identification of the lineage specific bone marrow cell adhesion molecule proteins can be used alone or in conjunction with CSF to treat such disorders.

The compositions for treatment of blood disorders in accordance with the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing the protein or peptide of the present invention or the antibody or binding portion thereof of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The bone marrow cell adhesion molecule proteins of the present invention and the antibodies raised by such proteins (or binding portions thereof) may also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For gene therapy regimes, the DNA molecules of the present invention are inserted into a vector and then introduced into appropriate host cells (e.g., hematopoietic cells). These cells are then introduced into a patient's bone marrow for therapeutic effect.

In yet another aspect of the present invention, the array of bone marrow cell adhesion molecule proteins identified supra can be used to diagnose blood disorders in humans. In this method, a sample of bone marrow cells are taken from a patient with a blood disorder, cultured in a monolayer and lysed to form a cell lysate. The lysate is centrifuged, and the pellet of cell nuclear material is discarded. The supernatant containing cell membranes is then centrifuged at high speed to form a membrane pellet. The pellet is solubilized in lithium dodecyl sulfate to form a solution. That solution is subjected to polyacrylamide gel electrophoresis to separate the cell adhesion molecule proteins by size and charge within the gel. The gel is then contacted with a blotting material to transfer the separated cell adhesion molecule proteins to the blotting material. Hematopoietic cells are then applied to the blotting material where they bind to the blotted cell adhesion molecule proteins. The blotting material is stained to detect the separated cell adhesion molecule proteins, by reaction with the added hematopoietic cells, and the stained blotting material is compared with a stained blotting material obtained from healthy bone marrow cells to determine whether there are any differences in cell adhesion molecule proteins. The step of solubilizing in lithium dodecyl sulfate can be preceded by solubilizing the pellet in 2% nonaethylene glycol octylphenol ether (i.e. Triton® X-100, available from Bio-Rad, Hercules, Calif.) solution to form a solution of cellular materials. The cellular materials are then centrifuged to form a further pellet which is then subjected to solubilization in the lithium dodecyl sulfate. The blotting materials and stains useful in this process are described infra with respect to the general method for detecting binding between cell adhesion molecule proteins and cells in accordance with the present invention.

Blood disorders can also be diagnosed in a sample of bone marrow cells by utilizing the above-described antibody or binding portion thereof. In accordance with this procedure, the sample is contacted with the antibody or binding portion thereof and any reaction between them, which indicates the presence of the protein raised by the antibody or binding portion thereof, is detected using an assay system.

The DNA molecule of the present invention can also be used for diagnostic purposes. For example, the DNA sequence of stromal cells in patients with blood disorders can be compared to those cells in healthy individuals for indication of genetic abnormality.

The assay system may have a sandwich or competitive format. Examples of suitable assays include an enzyme-linked immunosorbent assay, a radioimmunoassay, a gel diffusion precipitant reaction assay, an immunodiffusion assay, an agglutination assay, a fluorescent immunoassay, a protein A immunoassay, an immunoblotting assay, an immunoperoxidase assay, an immunoalkaline phosphatase assay, flow cytommetry, or an immunoelectrophoresis assay.

Another aspect of the present invention relates to a method for detecting binding between cell adhesion molecule proteins and cells generally.

In this process, a solid pellet containing cell adhesion molecule proteins from cell membranes is solubilized with lithium dodecyl sulfate to form a solution. The solution is subjected to polyacrylamide gel electrophoresis to separate the cell adhesion molecule proteins by size and charge within the gel. The gel is then contacted with a blotting material to transfer the separated cell adhesion molecule proteins to the blotting material. Such blotting is generally carried out at temperatures of 4° C. to 20° C., preferably 4° C. Cells having a potential to bind to the cell adhesion molecule proteins on the blotting material are then applied to the blotting material. The cell adhesion molecule proteins and the cells are next allowed to react to the blotting material. This procedure can be used either to detect and identify new, unknown cell adhesion molecule proteins with known cells applied to the blotting material or to detect unknown cells applied to the blotting material with known cell adhesion molecule proteins.

When starting with whole cells, the cells are lysed to form a cell lysate by sonication. Cell nuclear materials are then separated from the cell lysate to form a residual supernatant fraction. This is preferably carried out by low speed centrifugation at speeds of preferably 600 g. The nuclear pellet is discarded, and the residual supernatant fraction is centrifuged at high speeds of preferably 20,000 g to form the initial pellet containing cell membrane proteins and cell adhesion molecule proteins.

Where live, adhered cells are not desired, the blotting material is then stained to detect which proteins bind to the cells. The stained blotting material is then examined for indications of cell adhesion molecule proteins bound to cells. Prior to solubilizing in lithium dodecyl sulfate, the pellet can be solubilized in 2% nonaethylene glycol octylphenol ether (i.e. Triton® X-100) solution to form a solution of cellular materials. That solution is then centrifuged to form a further pellet which is next subjected to the step of solubilizing with lithium dodecyl sulfate. Centrifuging can be carried out at speeds of preferably 20,000 g.

The blotting material can be polyvinylidene difluoride, nitrocellulose, or nylon membranes. Polyvinylidene difluoride is preferred.

Staining is carried out with any number of stains, including propidium iodide, hexatoxylin, Wright/Giemsa stain, Papanicolau stain, and immunoperoxidase. Propidium iodide and hexatoxylin are preferred.

The cells which are lysed according to the above process in order to isolate cell adhesion molecule proteins can be varied greatly. For examples cells from the brain, lymph nodes, kidney, liver, etc. can all be treated by this process.

The cells applied to the blotting material prior to staining can also be varied widely. For example, suitable cells include hematopoietic cells or cells derived from the brain, lymph nodes, kidney, liver, etc. Alternatively, unknown mixtures of cells can be applied to the blotting material containing selected, known cell adhesion molecules in order to identify the types of cells in the mixture.

The process of the present invention can be terminated prior to staining in order to prevent cells adhered to cell adhesion molecule proteins on the blotting material from perishing. These cells can then be cultured on the blotting material or after elution from the blotting material. As a result, cells of interest can be isolated and cloned in a substantially pure state. The growth of the cells can then be studied in culture.

EXAMPLES

Lectins and Other Cell Adhesion Proteins.

Con A and PHA-L were purchased from Sigma (St. Louis, Mo.); and WGA was from Vector (Burlingame, Calif.); and placental ECM proteins were from Collaborative Biomedical Products (Becton Dickinson Labware, Bedford, Mass.). A sample of the recombinant soluble form of VCAM-1 (rs VCAM-1) was kindly provided by Dr. Roy Lobb (Biogen, Inc, Cambridge, Mass.). Lectins were reconstituted in 125 .mM Tris-HCl, pH 6.8. All samples were aliquoted and stored frozen at $-40°$ C.

Cell Culture.

All cell culture media were purchased from GIBCO-BRL (Grand Island, N.Y.). KG1a (myeloid precursor) and NALM-6 (B-lymphoid precursor) human cell lines were maintained in RPMI 1640/ 9% FBS/1% penicillin/streptomycin.

LDS-PAGE.

For "native" 4–12% discontinuous gradient mini gels (1 mm thick), the separating gel consisted of 12% T, 2.6% C, 0.375M Tris-HCl, pH 8.8, was made the day before use, and was allowed to stay all room temperature overnight. The stacking gel consisted of 4% T, 2.6% C, 0.125M Tris-HCl, pH 6.8 and was made 1–2 h before use. Precast "native" continuous gradient mini gels (1 mm thick, 4–20% T, 2.6% C, 0.375M Tris-HCl, pH 8.8) were purchased from Bio-Rad. Notably, both gels were "native" and contained no LDS (or SDS). The Bio-Rad Mini-PROTEIN II system was used for electrophoresis. The upper (or inner) chamber electrode buffer consisted of 25 mM Tris/192 mM glycine/1 mM EDTA/0.1% LDS, pH ~8.7. The lower (or outer) chamber electrode buffer consisted of 25 mM Tris/192 mM glycine, pH ~8.7, and notably contained no LDS (Delepelaire, P., and Chua, N. M., *Proc. Natl. Acad. Sci. USA* 76:111–115 (1979), which is hereby incorporated by reference). No acid or base was added to adjust the pH of the running buffers to avoid any conductivity/heating problems during electrophoresis (Bio-Rad. in Mini-PROTEAN II Ready Gels: Instruction Manual, P. 10, Bio-Rad Laboratories, Richmond, Calif. (1991)), which is hereby incorporated by reference. The running buffers were prechilled overnight on ice.

Samples were prepared for electrophoresis by mixing an equal volume of sample and 2x LDS-PAGE sample buffer (0.575% (w/v) LDS/20% glycerol in 125 mM Tris-HCl, pH 6.8). Thus all final samples contained 0.2875% LDS and 10% glycerol in 125 mM Tris-HCl, pH 6.8. No tracking dye was included in the samples. They were incubated on ice for 60 min prior to loading.

Approximately 200 ml of prechilled outer running buffer was added to the outer chamber; and approximately 115 ml prechilled inner running buffer was added to the inner chamber. Samples (35 ul per lane) were loaded and then the inner running buffer which would have warmed up to room temperature while loading the samples was drained using an appropriate siphon setup, and refilled with fresh prechilled inner running buffer. The outer chamber was also filled with prechilled outer buffer. Since the Mini-PROTEAN II electrophoresis unit does not have a cooling system, electrophoresis was conducted by placing the Mini-PROTEAN II tank in an ice/salt/water bath in a suitable size clear plastic container (Keepers Clear Box, 16"×11"×6", Rubbermaid, Wooster, Ohio). LKB 2103 Model power supply was used for running the electrophoresis at a constant voltage of 200 V.

The precast 4–20% gels were run for 45 min, with post-run temperature of inner chamber buffer rising up to $21°$ C. The 4–12% gels were run for 60 min, replacing inner chamber buffer once after 30 min. The post-run temperatures of inner chamber buffer rose up to $19°$ C. The outer chamber buffer temperatures remained at $~4°$ C. in either case. Thus, at no stage of the electrophoresis were the proteins exposed to a temperature higher than the room temperature. By contrast, in SDS-PAGE setup without the above precautions, the inner buffer temperature rose up to $50°$ C.

Coomassie Blue Staining of Gels.

Gels were stained using a "quick" procedure essentially as described (Pharmacia LKB., "Instruction Manual: ExcelGel Precast Gels and Buffer Strips for Horizontal SDS Electrophoresis," pp. 1–8, *Pharmacia LKB Biotechnoloqy*, Uppsala, Sweden (1989), which is hereby incorporated by reference).

Electrophoretic Protein Blotting.

Immobilon-P (a polyvinylidene difluoride (PVDF) membrane, 0.45 um) was purchased from Millipore (Bedford, Mass.). Mini Trans-Blot blotting apparatus, Bio-Ice cooling units and Model 200/2.0 power supply were from Bio-Rad. Transfer buffer consisted of 25 mM Tris/192 mM glycine pH ~8.7 (Towbin, H., Staehelin, T., and Gordon, J., *Proc. Natl. Acad. Sci. USA*, 76:4350–4354 (1989), which is hereby incorporated by reference). No acid or base was added to adjust the pH to avoid any conductivity/heating problems during blotting. Furthermore, the buffer contained no methanol or LDS (or SDS). It was pre-chilled overnight on ice. Two Bio-Ice cooling units were prepared in advance by filling with distilled water and freezing at $-20°$ C. Blotting was performed following the instructions accompanying the Mini Trans-Blot system and the Immobilon-P membrane. After wetting of PVDF membrane in absolute methanol for 1–3 sec, it was washed for 1–2 min in ddH$_2$O. The membrane was then equilibrated in cold transfer buffer for 30 min or longer in the refrigerator. The gels were equilibrated/washed in cold transfer buffer for exactly 30 min in the refrigerator. Transfer was performed for 60 min at 100 V (constant voltage), replacing the cooling unit once after 30 min. The final post-run temperatures were $~18°$ C. Starting current was ~210 mA and the finishing current at the end of 60 min was ~390 mA. After transfer, the membranes were routinely dried on paper towels at room temperature for approximately 30 min.

Coomassie Blue Staining of Protein Blots.

Staining of protein blots on PVDF was essentially as described (LeGendre, N., and Matsudaira, P., in "A Practical Guide to Protein and Peptide Purification for Microsequencing", (Matsudaira, P. T., Ed.), pp. 49–69, *Academic Press, San Diego* (1989), which is hereby incorporated by reference).

Cell Binding Assay on PVDF Protein Blots.

Bovine serum albumin (BSA) was obtained from Sigma (#A-4503) and the 10×phosphate-buffered saline with calcium (9 mM) and magnesium (5 mM) (PBS+), and without Ca$^{2+}$ and Mg$^{2+}$ (PBS-CMF), were obtained from GIBCO-BRL. The 1 ×PBS-CMF was prepared by simply diluting 10-fold with ddH$_2$O (pH 7.4, unadjusted) whereas the 1 ×PBS(+) required pH adjustment to 7.4 using 1N NaOH. Needed amounts of 1 ×PBSs and the BSA solutions (5% BSA/PBS(+); 1% BSA/PBS(+); and 0.5% BSA/PBS (+)) were prepared no earlier than a day before use and kept refrigerated until use. The 5% BSA/PBS(+) was prewarmed to room temperature prior to use.

Examples 1 to 11 describe a generalized procedure for isolation and detection of cell adhesion molecule proteins.

Example 1

Assay Chamber

Cell adhesion assay chambers (each 7 cm long ×5.5 cm wide ×1.75 cm deep) suitable for blots of 5 lanes wide (6 cm long ×4.5 cm wide) were constructed using plexiglass blocks of 9.6 cm ×8.1 cm ×2.3 cm size or using polycarbonate blocks of similar size (FIG. 1). The construction of the chambers was designed to optimize the cell density per unit area of the blot. It would also leave a room of 0.5 cm all around the blot to be able to handle the blot with forceps, accommodate a 30 ml cell suspension (occupying ~8 mm deep) and provide sufficient room above the suspension so that carrying them if needed would not be a problem.

Example 2

Blocking of Nonspecific Binding Sites on PVDF

Prior to blocking of nonspecific binding sites, the dry Immobilon-P membranes with protein blots were rewetted in absolute isopropanol (instead of absolute methanol) in a small plastic container for ~10 sec. Isopropanol was poured off and the membrane was washed in PBS(+) for 3×3 min (100 ml/wash) at room temperature by gentle manual rocking. Blocking involved incubating in 5% BSA/PBS(+) for 1 h at room temperature, followed by overnight incubation in 1% BSA/PBS(+) in the cold room (4° C.). With a fine curved forceps, the membrane was transferred from plastic container to a plexiglass cell adhesion assay chamber containing 30 ml of 5% BSA/PBS(+), making sure the protein side was up. The vessel was gently rocked (~10 rpm) during blocking on a rotator. After 1 h, the blocking solution was aspirated and the blot was washed in PBS(+) 3×3 min on the rotator (20 ml/wash). After the last wash, 30 ml of 1% BSA/PBS(+) was added, and the vessel was covered with a large plastic container and incubated in the cold room overnight with no rocking. As could be observed from the side of the vessel, sometimes especially after transfer from our 4–12% gels, the Immobilon-P tended to curl up like an "arch". Whereas such distortion of membrane may be inconsequential in western blotting, it must be straightened prior to cell blotting. This could be done by lifting one end of the membrane from the BSA solution using a fine curved forceps, and gently bending on itself twice or thrice to reverse the arch or the curl. The membrane would then remain flat during the entire procedure. Regardless of the final cell adhesion assay temperature, the blocking procedure remained same.

Example 3

Cell Adhesion Assay

Cell adhesion to protein blots was investigated at 4° C., room temperature and 37° C. The reasons for the use of three different assay conditions are discussed infra.

a) Cell Adhesion Assay at 4° C.

Target cells were washed once in PBS-CMF by centrifugation, resuspended in 30 ml of 1% BSA/PBS(+), counted (~3×10$^6$/ml), and stored on ice until the blot was ready for cell incubation. Following overnight incubation of the blot, the blocking solution was removed and the blot was washed in cold 0.5% BSA/PBS(+) for 3×5 min with gentle rocking during the first two washes and with no rocking during the last wash. During the last wash and prior to the addition of cells, it was again checked to see that the membrane remained flat at the bottom of the vessel. The last wash solution was removed; the blot was centered in the vessel with a fine curved forceps; cell suspension was mixed with a 10 ml pipet and then slowly added to the center of the blot avoiding any air bubbles. The vessel was covered with a large plastic container and incubated in the cold room (4° C.) for 90 min for the cells to settle on the blot and adhere to the specific protein bands. At the end of cell incubation, the vessel was brought out of the cold room, slightly lifted and tilted to a corner, and the cell suspension was aspirated from the corner using a 25 ml pipet. Then blots were washed 3×5 min using cold 0.5% BSA/PBS(+) at room temperature. To minimize turbulence, all washes were added using a 25 ml pipet (20 ml/wash) by placing the pipet tip to the side of the chamber and were aspirated from a corner by tilting of the vessel so that all fluid was removed. After aspirating each wash, the blot was gently pushed to one end of the chamber with a fine forceps and then fresh wash solution was added to the chamber away from the blot. This washing procedure was found to be optimal; and no rocking of the vessel was attempted during the procedure. Thus simply adding and removing the wash solution was adequate to remove all the nonadherent cells and provide a clean background.

b) Cell Adhesion Assay at Room Temperature

This was similar to the assay at 4° C., except that all solutions were maintained and all steps were conducted at room temperature. Washes were similar to those under the assay at 4° C., except that 0.5% BSA/PBS(+) solution was maintained at room temperature, and the assay chamber was gently swirled ×3 after adding and before aspirating each wash to obtain clean background. For some cell types, it was necessary to supplement this washing procedure by gently rocking the assay chamber ×3 after adding and before aspirating each wash.

c) Cell Adhesion Assay at 37° C.

Prior to cell incubation, blots were washed using 5% FBS/PBS(+) instead of 0.5% BSA/PBS(+). Then cell incubation was carried out at 37° C. (i.e., in a standard tissue culture incubator) for 60 min in 5% FBS/RPMI 1640 instead of 1% BSA/PBS(+). A 5% FBS/PBS(+) solution prewarmed to 37° C. instead of 0.5% BSA/PBS(+) was used as the post-cell incubation washing medium. The 3×5 min washing incubations were carried out in a 37° C. oven, and the assay chamber was gently swirled ×3 after adding and before aspirating each wash as above.

At the end of last wash, most but not all of the solution was aspirated; then using a fine curved forceps the membrane was gently transferred from cell incubation chamber to an adjoining small plastic vessel containing ~100 ml of 10% neutral buffered formalin. The blot was fixed for 2 h at room temperature.

It may be mentioned that by the end of cell incubations, cells settled on the blots leaving on top clear media. In contrast to previous reports (Wong, H-J., Aubin, J. E., Wasi, S., and Sodek, Jr., *Biochem. J.* 232:119–123 (1985), which is hereby incorporated by reference), no "smudge" or clumps of cells were observed at any temperature of the present assay.

Example 4

Propidium Iodide Staining of Cell Bands on PVDF Blots

PI was purchased from Sigma. Stock (20×) solution was prepared under a chemical hood by dissolving 10 mg in 100 ml of filter-sterilized PBS-CMF. The stock solution was stored in the refrigerator wrapped with aluminum foil. Working solution (0.5 mg/100 ml) was prepared as needed (250 ul stock +4.75 ml PBS-CMF). The staining procedure was performed at room temperature under the hood. After fixation, the formalin was poured off; the membrane was washed 3×3 min in cold PBS (+) (100 ml/wash, added with a 100 ml cylinder); after each wash the solution was poured off. After the second washing, to avoid sticking and to facilitate easy transfer of membrane, most but not all of the wash solution was removed and using a fine forceps the membrane was transferred to another plastic container, used only for PI. One more wash was performed in this vessel followed by removal of all of the wash solution which was poured off into a waste beaker. One to 2 ml of 1×PI solution was then laid over the membrane with a Pasteur pipette making sure that the entire membrane was covered with the PI solution. After 10 min incubation, the PI solution was aspirated with a Pasteur pipette and transferred to the waste container. The membrane was washed 3×3 min in cold PBS (+) (100 ml/wash).

The cell bands on wet blots when viewed under long wave UV light appeared as faint orange fluorescent bands. However, they would become very strong and sharp after drying of the membrane. The blots were therefore dried on paper towels and stored in thin (1.15 MILS) plastic bags in the refrigerator. Intensity of PI-positive bands remained undiminished even after storage for months. Bands were visualized using a hand-held long wave (366 nm) UV light source (MODEL UVL-56, BLAK-RAY LAMP, UVP, Inc, San Gabriel, Calif.). The blots contained in the plastic bags were photographed using a cardboard box equipped with a similar UV light source, a light red contrast filter (Davis, B. J., *Ann. N.Y. Acad. Sci.* 121:404–427 (1964), which is hereby incorporated by reference), Kodak Technical Pan Film and a Polaroid MP3 camera with a 135 mm lens. The bellows extension was 8" and the exposure time was 2 min at F8. The film was processed in a Kodak Versamat Model 5 at 2 FPM in Duraflo RT developer at 80° F.

Photomicrographs were taken using a fluorescence microscope (Olympus BHS) equipped with epi-illumination and UV excitation filter (UG1). No clearing of the membrane was required for microscopic examination of the adherent cells using epifluorescent illumination. In view of PI's potential carcinogenicity, it was easier to handle a PI-stained blot by keeping it within the plastic bag; it was also not necessary to take it out during microscopy. The bag was laid over a large glass slide; a large coverglass was laid over the bag pressing the bag such that the entire blot was in one plane; the bands were readily located by moving the blot under a 10× objective. Photomicrographs were taken using both 10× and 20× objectives.

Example 5

Hematoxylin staining of cell bands on PVDF blots

Stain A is a strong Harris-type hematoxylin stain—the Hematoxylin-2, and related Clarifier-2 (a dilute acetic acid) and a bluing agent. (a buffered solution with an alkaline pH) were purchased from Richard-Allan (Kalamazoo, Mich.). Stain B is a hematoxylin stain of Gill's formulation #1 which was purchased from Fisher Scientific. After fixation in 10% formalin, the blot was transferred to a fresh plastic container and stained sequentially by Stain A and Stain B by gently adding and pouring off appropriate amounts of respective solutions. The Stain A procedure was as follows: 1) Stained in Hematoxylin-2 for 30 sec; 2) Rinsed in ddH$_2$O for 45 sec; 3) Destained in Clarifier-2 for 30–60 sec; 4) Rinsed in ddH$_2$O for 45 sec; 5) Developed in bluing agent for 60 sec; and 6) Rinsed in ddH$_2$O for 45 sec. This stain alone was sufficient for macroscopic visualization of blue cell bands with a clean white background. When microscopic visualization of individual cells was desired, additional staining was performed using Stain B. The Stain B procedure was as follows: 1) Stained in Gill's #1 Hematoxylin for 10 min; and 2) Washed in tap water ×2 over 5 min. The blot was laid over a large glass slide or plate and viewed under a standard transmission light microscope while still wet. No special clearing of membrane or mounting in Permount or coverslipping was required. Finally, the blot was dried over paper towels and stored in a thin plastic bag in the refrigerator. Any time microscopic visualization was desired, the membrane was rewet in absolute methanol for 2–3 sec, rinsed 2–3×in ddH$_2$O, laid over the glass plate, and viewed under the microscope.

Example 6

Fractionation of Proteins by LDS-PAGE Mini Gels

Figure 2A:
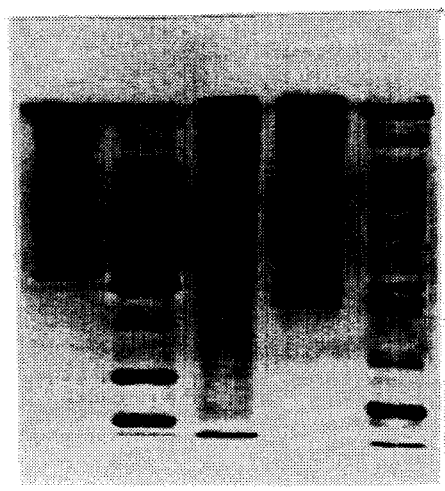
FIGS. 2A–B show a comparison of resolving patterns of proteins fractionated by LDS-PAGE, using a 4–12% discontinuous gradient gel in FIG. 2A, and using a 4–20% continuous gradient gel in FIG. 2B. Samples were as follows: lane 1, PHA; lane 2, Con A; lane 3, ECM proteins; and lane 4, WGA. Quantity of material loaded in each lane was 10 ug, except for WGA which was 40 ug. No attempt was made to determine the actual protein content of the samples loaded. All final samples contained 0.2875% LDS and 10% glycerol in 125 mM Tris-HCl, pH 6.8, and were loaded as 35 ul/lane. Molecular weight standards are shown in lane 5. Gels were stained by Coomassie Blue. Corresponding lanes in gel A and gel B were loaded with identical protein samples; accordingly, protein band patterns in matching lanes are to be compared, i.e. band pattern in lane 1 of gel A with that in lane 1 of gel B, and so on. Note high molecular weight protein bands in 4–12% discontinuous gradient gel represent multimeric complexes. Such HMW bands are absent or markedly decreased in 4–20% continuous gradient gel, whereas low molecular weight bands representing the monomeric units are noteworthy. This observation is most notable with PHA (lanes labeled 1) and WGA (lanes labeled 4).
Figure 2B:

Present studies were conducted using 4–12% discontinuous gradient and 4–20% continuous gradient mini gels. As shown in FIG. 2A and FIG. 2B, both gel systems provided excellent resolution of protein bands with some significant differences. For example, HMW protein bands are seen in the 4–12% discontinuous gradient gel representing multimeric complexes, whereas they are absent or markedly decreased in the 4–20% continuous gradient gel. On the other hand, LMW bands representing the monomeric units are noteworthy in the latter gel. This finding is best illustrated when the resolving patterns of PHA and WGA are compared. Thus the 4–12% gels tended to favor or preserve multimeric complexes whereas 4–20% gels resolved them into monomeric units. Similar results were obtained with BM stromal cell membrane protein mixtures. These results suggest that the absence of LDS in the gel and lower reservoir buffer (as is the case in 4–20% continuous gradient gel) is not sufficient for preservation of multimeric complexes during LDS-PAGE. The stacking portion of the discontinuous gradient gel has the capacity to concentrate the sample proteins: into a narrow zone prior to separation by the resolving gel. (Ornstein, L., *Ann. N.Y. Acad. Sci.,* 121:321–349 (1964); Davis, B. J., *Ann. N.Y. Acad. Sci.,* 121:404–427 (1964), which are hereby incorporated by reference). Therefore, the stacking of sample proteins would also seem to play a part in the preservation of protein complexes. This conclusion was further substantiated using a precast single percentage (12%) gel without stacking (Bio-Rad) which failed to preserve the multimeric protein complexes (data not shown).

Example 7

Electrophoretic Protein Blotting

Figure 4A:
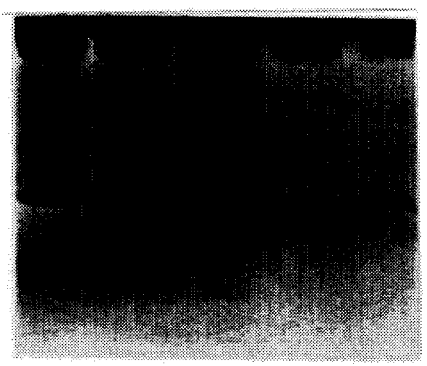
FIGS. 4A–D show cell adhesion to protein bands representing multimeric complexes of PHA separated by LDS-PAGE using a 4–12% discontinuous gradient mini gel, and blotted onto PVDF membrane. Decreasing amounts of PHA (20 µg, 10 µg, 5 µg, 2.5 µg and 1.25 µg) were prepared in a sample buffer consisting of 0.2875% LDS and 10% glycerol in 125 mM Tris-HCl, pH 6.8, and were loaded as 35 µl/lane.
Figure 4B:
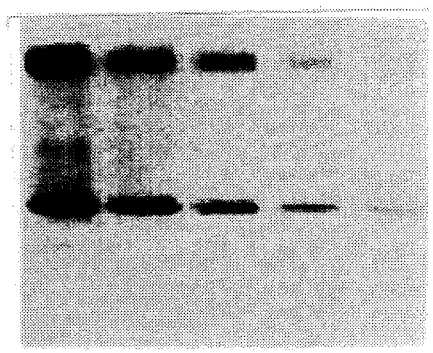
Figure 4C:
Figure 4D:
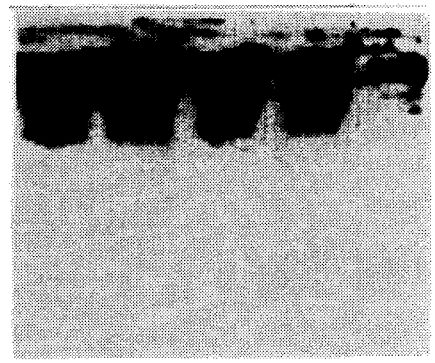
Figure 5A:
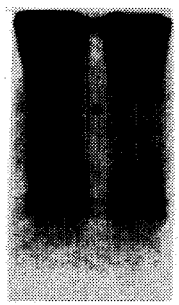
FIGS. 5A–D show cell. adhesion to protein bands representing multimeric complexes of WGA separated by LDS-PAGE using a 4–12% discontinuous gradient mini gel, and blotted onto PVDF membrane. Decreasing amounts of WGA (40 µg and 20 µg) were prepared in sample buffer consisting of 0.2875% LDS and 10% glycerol in 125 mM Tris-HCl, pH 6.8, and were loaded as 35 µl/lane.
Figure 5B:
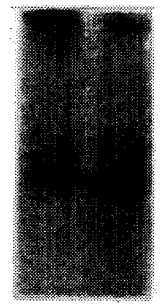
Figure 5C:
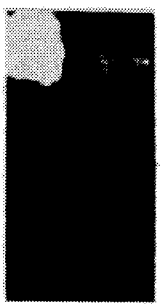
Figure 5D:
Figure 6A:
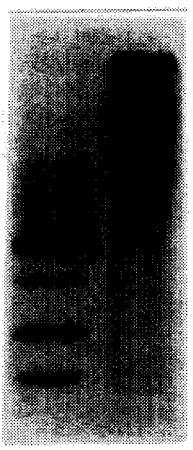
FIGS. 6A–B show cell adhesion to Con A and placental ECM adhesion proteins fractionated by LDS-PAGE using a 4–12% discontinuous gradient mini gel, and blotted onto PVDF membrane. Samples were as follows: lane 1, Con A.10 µg; and lane 2, ECM 10 µg.
Figure 6B:
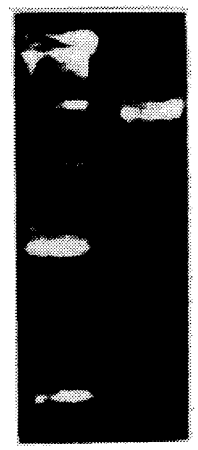
Figure 7A:
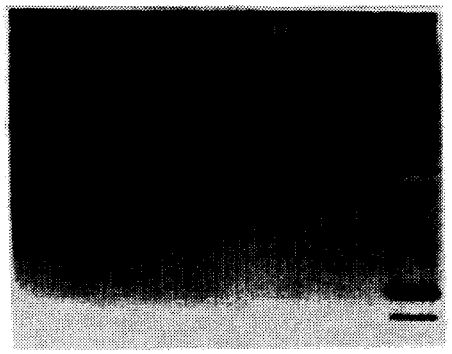
FIGS. 7A–C show cell adhesion to VCAM-1 protein separated by LDS-PAGE using a 4–12% discontinuous gradient mini gel, and blotted onto PVDF membrane. Decreasing amounts of rs VCAM-1 (2.5 µg, 1.25 µg, 0.62 µg, 0.31 µg and 0.15 µg) were prepared in a sample buffer consisting of 0.2875% LDS and 10% glycerol in 125 mM Tris-HCl, pH 6.8, and were loaded as 35 µl/lane.
Figure 7B:
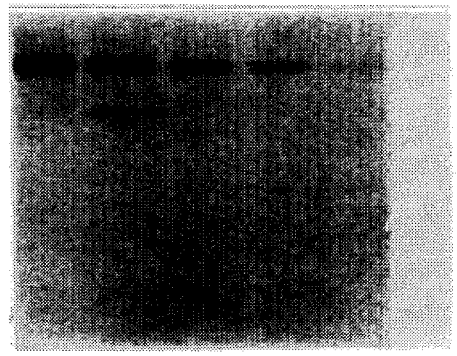
Figure 7C:
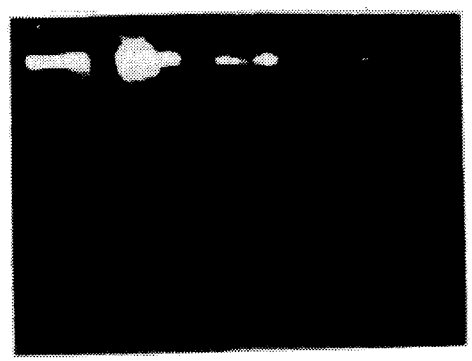

Tank blotting was used in the present study for two reasons, a) it permitted cooling while blotting as well as monitoring of buffer temperature, and b) it provided more complete transfers than a semi-dry blotting method (data not shown). Protein patterns of gels and corresponding blots compared very favorably (compare FIG. 4A and FIG. 4B). Efficiency of transfer also depended on the individual proteins, for example, PHA, Con A, and VCAM-1 transferred completely under the blotting conditions described here, whereas WGA transferred with much difficulty as judged by FIG. 5A and FIG. 5B and staining of gels following transfer. Notably, the blotting buffer consisted of standard Tris-glycine buffer (with pH ~8.7) and contained no LDS or SDS or methanol.

A major clue to the functioning of the present assay system has come from a fortuitous observation. Following protein blotting, blots are routinely dried at room temperature for 30 min on paper towels. After partial drying of the membrane it was observed that detergents were visible as chalky white bands at the buffer front especially in lanes containing both Triton® X-100 and LDS or CHAPS and LDS, requiring no special staining to detect them. Such chalky material was not observed in completely wet or completely dry blots, nor in any lanes above the buffer front area at any time. The material could be verified as due to detergents by dot-blotting of detergent-containing solutions on PVDF and observing them while they were drying (and documenting by photocopying). There was a positive correlation between the diameter of the chalky white dot and the concentration of detergent. Earlier studies (attempting to remove detergents from sample proteins to renature them) showed similar results on the NC paper; furthermore, the chalky white material would not, be seen if the samples had been treated with a detergent-binding resin such as Calbiosorb (Calbiochem, San Diego, Calif.) before dot-blotting on NC. These observations indicate that detergents contained in samples (i.e, Triton® X-100/LDS, and CHAPS/LDS) and the sample proteins had been separated on the gel during electrophoresis and the detergents had focused at the buffer front. A similar detergent band, especially when LDS was loaded excessively and electrophoresis was conducted at 25° C., was observed at the buffer front in LDS-PAGE gels by previous investigators (Kubo, K., and Takagi, T., *Anal. Biochem.*, 156:11–16 (1986), which is hereby incorporated by reference) after staining of the gels with a cationic surfactant (Takagi, T., Kubo, K., and Isemura, T., *Anal. Biochem.*, 79: 104–109 (1977), which is hereby incorporated by reference). Further investigations confirmed my earlier observations that detergents when present in samples as mixed micelles (Triton® X-11/LDS or CHAPS/LDS) migrated to the buffer front and subsequently transferred to PVDF blot (see FIG. 3B and FIG. 3C). This may be analogous to the mixed-micelles of NP-40/SDS formed during isoelectric focusing of the samples solubilized in NP-40/SDS (i.e., during the first dimension gel of the O'Farrell two-dimensional gel electrophoresis), where the detergent micelles migrate through the gel and focus at the acidic end of the gel (Ames, G. F-L. and Nikaido, K., *Biochemistry* 15: 616–623 (1976); O'Farrell, P. H., *J. Biol. Chem.* 250: 4007–4021 (1975), which are hereby incorporated by reference). On the other hand, LDS, in the absence of other detergents and under cold conditions, remained bound to polyacrylamide and failed to transfer to PVDF (FIG. 3B), the result being that protein bands on PVDF blot are automatically "cleared" of detergents, requiring no separate detergent removal procedure (see below). Such electrophoretic removal of detergents from sample proteins may be unique to a gel system such as present one which does not contain LDS in the gel and the lower reservoir buffer and, as discussed later, may be important in causing renaturation of proteins and preservation or restoration of cell adhesion function of CAMs. In contrast, if the gel system is saturated with LDS by including LDS in the gel and the lower reservoir buffer (Kubo, K., and Takagi, T., *J. Biochem.* 99:1545–1548 (1986); Kubo, K., and Takagi, T., *Anal. Biochem.* 156:11–16 (1986), which are hereby incorporated by reference), the sample proteins would not be "cleared" of the detergent and would remain dissociated and denatured. Therefore, the choice of electrophoretic conditions seems to have played a crucial role for success of the present technique.

Example 8

Cell Adhesion to Protein Bands on PVDF

Since cell-cell and cell-ECM interactions are physiologically relevant, cell adhesion assay on protein blots represents a functional assay. However, proteins are often denatured in SDS-PAGE and may not be detected by cell blotting. Protocols for renaturation of SDS-denatured proteins blotted onto NC or PVDF have been described (Celenza, J. L., and Carlson, M. *Methods in Enzymology* (Hunter, T., and Sefton, B. M., Eds.), Vol. 200, pp. 423–430, Academic Press, San Diego (1986); Ferrell, Jr., J. E., and Martin, G. S. *Methods in Enzymology* (Hunter T., and Sefton, B. M., Eds.), Vol. 200, pp. 430–435, Academic Press, San Diego (1986), which are hereby incorporated by reference). Some such procedures involve further denaturation of blotted proteins with guanidine hydrochloride followed by a gradual renaturation using buffers containing nonionic detergents, such as NP-40. However, initial studies show that the use of renaturation or blocking buffers containing 0.1% NP-40 or 0.05% Tween 20 caused extensive nonspecific adherence of certain cell types, for example NALM-6 and Ramos, to the background. These and other related difficdlties provided the impetus for the development of the present technique with a built-in renaturation mechanism which requires no separate renaturation procedure (see above).

Cleanest results were obtained when the adhesion assay was performed at 4° C. with virtually no background adherence of cells. However, the assay at 4° C. does not reflect physiological conditions and was found to be not as sensitive as at room temperature or 37° C. Furthermore, cell adhesion involving certain integrin molecules are abolished at 4° C. (Seth, R., Salcedo, R., Patarroyo, M., and Makgoba, M. W., *FEBS Letters* 282:193–196 (1991), which is hereby incorporated by reference). On the other hand, when the assay was performed at room temperature or 37° C., there was extensive nonspecific adherence to the background by some cells, for example, NALM-6. Use of 5% FBS instead of 1% BSA in the cell incubation medium prevented the problem of nonspecific adherence of cells to the background. However, FBS cannot be used when CAMs of interest are lectins since serum glycoproteins will compete with cellular glycoproteins and may inhibit cell adhesion to lectins. In the cell adhesion assay at room temperature involving lectins, the cell incubation medium and pre- and post-cell incubation washes used either PBS(+) alone or PBS(+) containing 1% or 0.5% BSA as indicated. Assay conditions were empirically determined for each cell type depending on adhesion molecule type.

Example 9

Propidium Iodide Staining of Cell Bands on PVDF

PI, a nucleic acid intercalating dye with excitation maxima of 342 nm and 495 nm, was investigated as a possible general stain for nucleated cells adherent on PVDF. Initial studies showed that the PI did not bind to PVDF itself, but tended to bind to BSA coated on PVDF causing some background staining. It was reasoned that since PI is a positively charged molecule (Ormerod, M. G., in "Flow Cytometry: A Practical Approach," (Ormerod, M. G., Ed.), pp. 29–44, IRL Press at Oxford University Press, Oxford, England (1990), which is hereby incorporated by reference), saturating BSA with a positive charge prior to PI staining would be a possible way to preventing binding of PI to the background. In this regard, it is notable that BSA functions as physiological carrier protein for inorganic ligands including $Ca^{2+}$ and $Mg^{2+}$, (McPherson, R. A., *Clinical Diagnosis and Management by Laboratory Methods* (Henry, J. B.; Ed.), 17th ed., p. 209, W. B. Saunders, Philadelphia (1984), which is hereby incorporated by reference). Therefore, these positively charged ions would be the ideal agents to block the BSA coating. Accordingly, the blot was washed in PBS(+) ×3 before and ×3 after PI staining, thus providing a clean background.

Figure 8A:
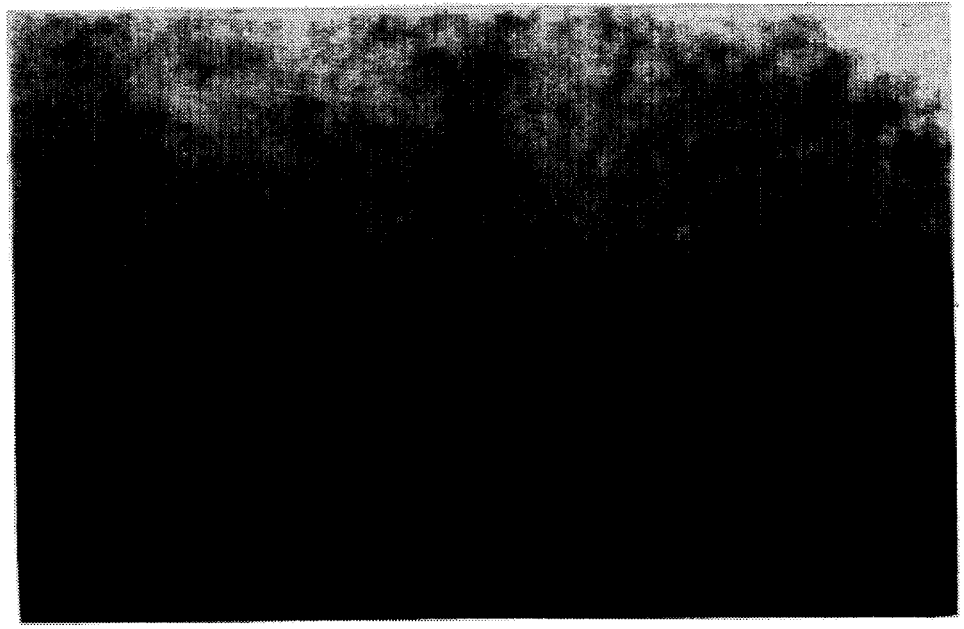
FIGS. 8A–B are photomicrographs of KG1a cells adherent to a PHA protein band on PVDF membrane, stained by PI. Blots were viewed under a fluorescence microscope with epi-illumination and a UV excitation filter without clearing of the membrane.
Figure 8B:
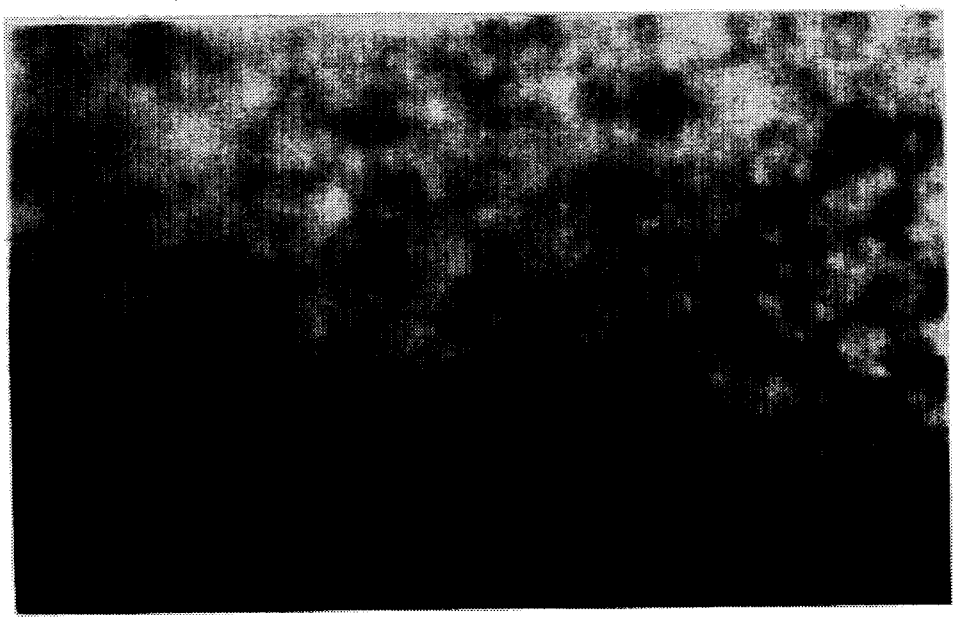

It is necessary that the cells be fixed prior to PI staining since PI will not enter live cells. While 70% ethanol was an effective fixative and a permeabilizing agent (Clevenger, C. V., and Shankey, T. V., *Clinical Flow Cytometry: Principles and Application* (Bauer, K. D., Duque, R. E., and Shankey, T. V., Eds.), pp. 157–175, Williams & Wilkins, Baltimore (1993), which is hereby incorporated by reference), it tended to fragment and detach cell bands. Therefore, cell blots were routinely fixed in 10% neutral-buffered formalin which provided adequate fixation in terms of stabilizing the cell bands as well as subsequent staining. The PI-positive bands were macroscopically visualized by viewing under a long wave UV light (366 nm). For microscopic visualization of individual adherent cells, a fluorescence microscope equipped with epi-illumination and a UV excitation filter was used., requiring no clearing of the membrane. Since wet blots were dimly fluorescent, only dry blots were routinely examined under the microscope (FIG. 8.). The granular architecture of the membrane apparent in the background is consistent with the open porous structure of the PVDF membrane (Pluskal, M. G., Przekop, M. B., Kavonian, M. R., Vecoli, C., and Hicks, D. A., *Bio Techniques* 4:272–282 (1986), which is hereby incorporated by reference), and does not represent unstained cells.

Example 10

Hematoxylin Staining of Cell Bands on PVDF

Figure 9A:
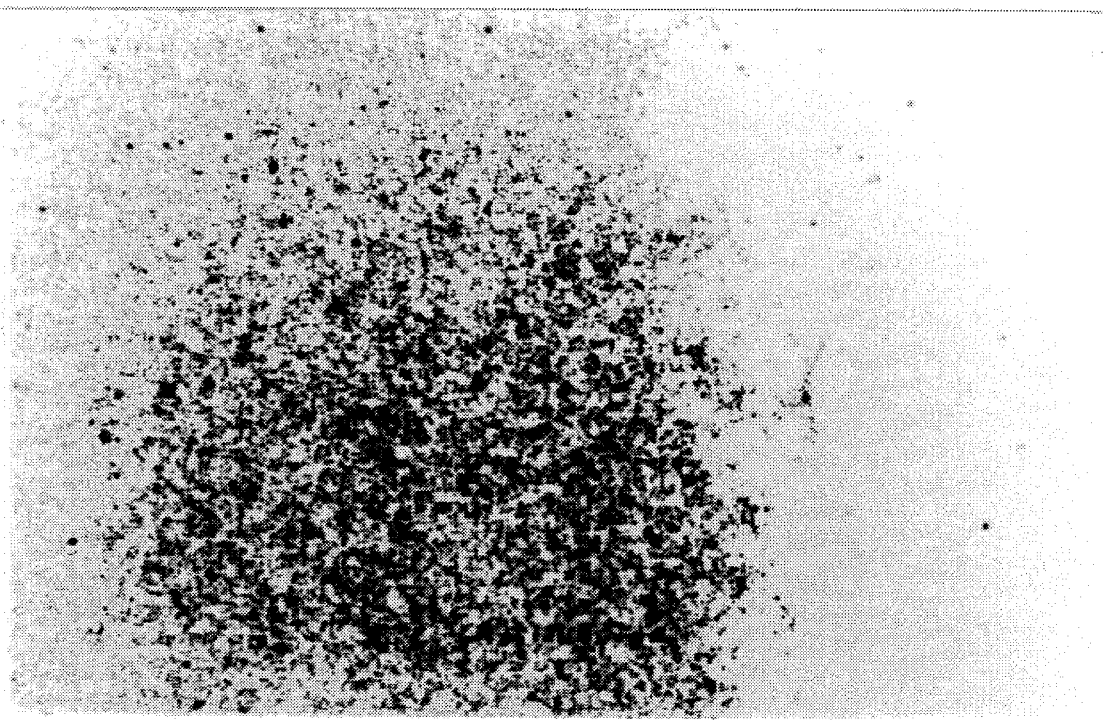
FIGS. 9A–B show photomicrographs of KG1a cells adherent to a PHA protein band on a PVDF membrane, stained by hematoxylin Stain A, then followed by Stain B. Blots were viewed under a standard transmission light microscope. No clearing of the membrane was necessary to view the cells under a standard light microscope.
Figure 9B:
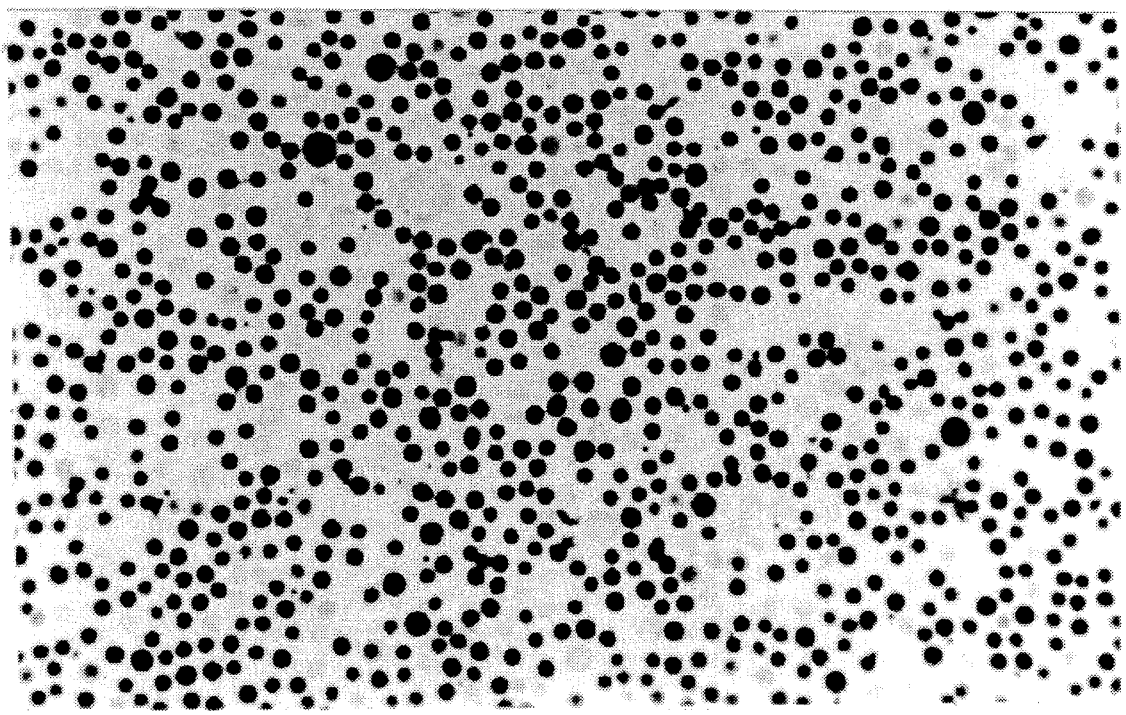

Several different hematoxylin stains and protocols were tested. Staining with *Hematoxylin*-2 after alcohol fixation was quite sufficient in terms of staining intensity and quality. Since alcohol fixation tended to fragment and detach cell bands, formalin fixation was routinely used in the present study. While staining with Hematoxylin-2 alone or Gill's #1 hematoxylin alone after fixation in formalin was adequate for macroscopic visualization of cell bands, neither stain was adequate for microscopic visualization of individual cells due to lack of uniform staining of the cells. Furthermore, Gill's stain showed an exaggerated granular architecture of the background membrane causing a confusing microscopic picture. A combined hematoxylin stain after formalin fixation provided the best alternative. The cells stained strongly and uniformly and the background was very smooth. Although the dry blots were difficult to view due to poor transmission of light, the wet blots showed excellent transmission of light facilitating a simple and unequivocal identification of the adherent cells against a smooth background. Therefore, the combined hematoxylin stain followed by viewing of the wet blots was the method of choice for microscopic visualization of the adherent cells. The combined stain was also interesting for another reason since it not only stained the bands with cells attached, but faintly stained the underlying protein bands as well, thus providing the protein band pattern in the background. It must be stated that this feature did not present a problem because the bands with adherent cells macroscopically appeared distinctly granular and raised as opposed to the bands with no cells attached which appeared smooth and flat. Further, the adherent cells could be readily verified by a quick "peek" under microscope requiring no clearing of the membrane (see FIG. 9). It facilitated easy and immediate identification of the protein bands exhibiting cell adhesion. Whereas hematoxylin stain allows quick and easy microscopic verification of adherent cells but may stain traces of gel at the top of blot, which may be misleading if not checked under microscope. PI stain does not present such a problem but it requires observance of safety precautions and requires a fluorescence microscope with epi-illumination for visualization of individual cells. No complex methods such as radiolabeling of target cells (Campbell, A. D., Long, M. W., and Wicha, M., *Nature* 329: 744–746 (1987), which is hereby incorporated by reference) or scanning electron microscopy of blots (Isberg, R. R., and Leong, J. M., *Proc. Natl. Acad. Sci. USA* 85: 6682–6686 (1988), which is hereby incorporated by reference) were necessary to detect or confirm cell adhesion.

Example 11

Cell Adhesion to Known CAMs on PVDF

Since lectins bind to cells (via cell-surface glycoproteins) and are commercially available, they were selected as model cell adhesion proteins to investigate cell blotting assay. Experimental conditions affecting protein electrophoresis, blotting, and cell adhesion were investigated and standardized using various plant lectins such as Con A, PHA, and WGA (Goldstein, I. J., Poretz, R. D., *The Lectins: Properties, Functions, and Applications in Biology and Medicine* (Liener, I. E., Sharon, N., and Goldstein, I. J., Eds.), pp. 33–247, *Academic Press*, Orlando (1986), which is hereby incorporated by reference), as well as the placental ECM adhesion proteins (Kleinman, H. K., in Collaborative *Biomedical Products Catalog*, P. 36, Bedford, Mass. (1991), which is hereby incorporated by reference). A known physiologically relevant cell adhesion protein, i.e., VCAM-1, kindly provided by Dr. Roy Lobb (Osborn, L., Hession, C., Tizard, R., Vasallo, C., Luhowskyj, S., Chi-Russo, G., and Lobb, R., *Cell* 59:1203–1211 (1989), which is hereby incorporated by reference), was also tested to verify whether its cell adhesion function was retained by the system. The KG1a (myeloid precursor), and the NALM-6 (lymphoid precursor) human cell lines were used as the target cells in the cell adhesion assay. Under the conditions described, all types of CAMs that were tested, i.e. lectin proteins including Con A, PHA, and WGA, and ECM proteins as well as VCAM-1 retained cell adhesion properties and showed cell binding (FIG. 4C, FIG. 4D, FIG. 5C, FIG. 6B, and FIG. 7C). In cases of PHA and WGA, mostly protein bands representing multimeric complexes showed cell adhesion; on the other hand, in the case of Con A, protein bands representing not only monomeric units but even fragments (i.e., LMW bands) exhibited cell binding. The assay is extremely sensitive as evident from the observation that VCAM-1, loaded as low as 0.3 μg per lane, produced a clearly delineated cell band. In case of PHA and WGA, clear cell bands were evident even when no protein bands were detectable on PVDF blot by Coomassie Blue staining. As can be expected, some CAMs are more adhesive than others. These results provide cell blotting a new and solid footing.

Figure 3A:
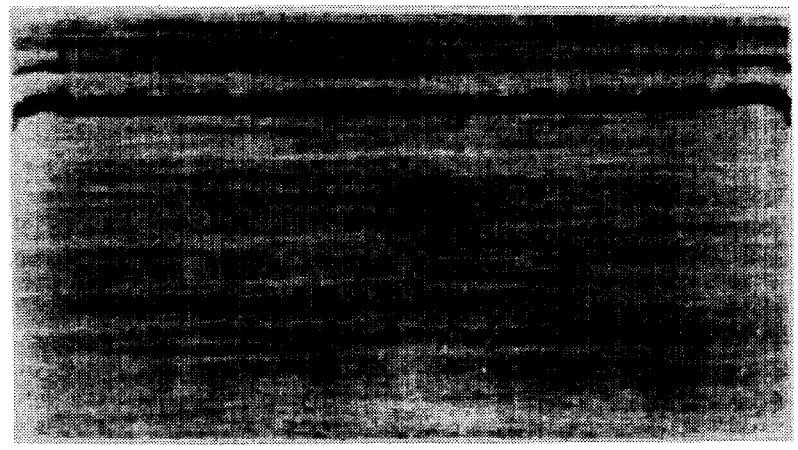
FIGS. 3A–C shows the removal of detergents from sample proteins during LDS-PAGE and subsequent blotting.
Figure 3B:
Figure 3C:
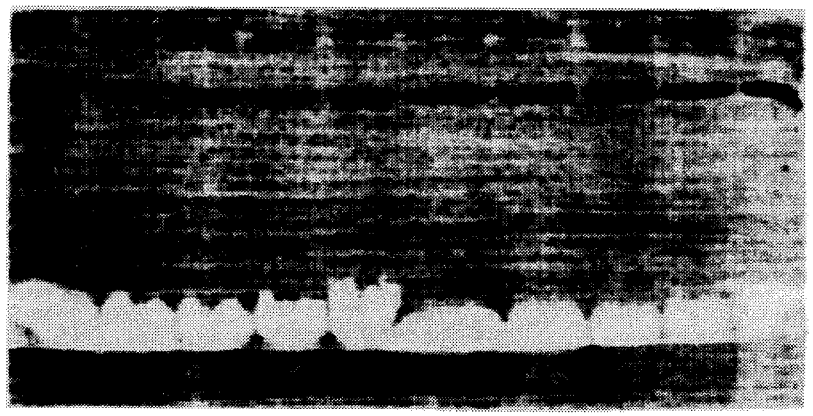

Several possible explanations may be considered for the positive results obtained by this new technique (FIG. 4C, FIG. 4D, FIG. 5C, FIG. 6B, and FIG. 7C), with respect to the preservation of cell adhesion function of proteins as follows. Thermal denaturation is prevented since sample proteins are never exposed to temperatures higher than the room temperature. Functional protein complexes are most likely preserved, especially by the 4–12% discontinuous gradient gels probably due to the stacking phenomenon (compare FIG. 2A and FIG. 2B) as well as the absence of LDS in the gel and the lower reservoir buffer (Delepelaire, P., and Chua, N. M., *Proc. Natl. Acad. Sci. USA* 76: 111–115 (1979)); Kubo, K., and Takagi, T., *J. Biochem.* 99: 1545–1548 (1986), which are hereby incorporated by reference). LDS has a high binding affinity for polyacrylamide at 4° C., which may cause a relative deficiency of LDS in the frontal region of the gel thus leading to accelerated migration of the LMW proteins in a relatively LDS-free gel segment (Kubo, K., and Takagi, T., *Anal. Biochem.* 156:11–16 (1986), which is hereby incorporated by reference); consequently proteins may be significantly "cleared" of LDS by the end of electrophoretic run. Since subsequent protein blotting is also performed under cold conditions, LDS would remain bound to polyacrylamide and not transfer to PVDF (FIG. 3B); on the other hand, LDS, when present in the form of mixed micelles involving for example Triton ® X-100, would migrate to the buffer front and transfer to PVDF (FIG. 3B and FIG. 3C). The net result in either case would be "clearing" of proteins of detergents by the end of protein blotting but prior to cell adhesion assay. Finally, since LDS is soluble even at 4° C., any remaining LDS would have been readily washed away during the two blocking steps (1 h at room temperature and overnight at 4° C.) and the multiple washing steps prior to the cell adhesion assay, leading to renaturation of the proteins and restoration or preservation of their cell adhesion functions.

In summary, the present technique is sensitive, specific and robust and should therefore lend itself for routine application in the investigation of novel CAMs. Cell blotting may not only provide the most direct approach possible for identifying CAMs but may also be capable of identifying adhesion proteins not detectable by other protein isolation techniques such as the conventional immunoprecipitation technique. Approximately fifty CAMs have so far been described (Pigott, R., and Power, C., *The Adhesion Molecule FactsBook*, Academic Press, San Diego (1993), which is hereby incorporated by reference), but it is reasonable to assume that many more such molecules remain unknown. It is hoped that this new technique would contribute to the growing list of these biologically important molecules.

Examples 12 to 22 relate to the isolation and analysis of cell adhesion molecules for bone marrow as follows.

Example 12

Cell Culture Preparation

Dexter-type stromal cell cultures were grown, as described in Dexter T. M., Allen T. D. and Lajtha L. G., *J. Cell Physiol.* 91:335 (1977); Gartner S. M. and Kaplan H. S., *Proc. Natl. Acad. Sci. USA* 77:4756 (1980), which are hereby incorporated by reference, from bone marrow samples obtained from normal adult donors with informed consent. The stromal cell cultures were set up using CD34-negative subset of bone marrow light density cells obtained after an immunoaffinity column separation (Berenson R. J., Andrews R. G., Bensinger W. I., Kalamasz D., Knitter G., Buckner C. D., Bernstein I. D., *J. Clin. Invest.* 81:951 (1988), which is hereby incorporated by reference), plating approximately 33–55×10$^6$ cells per T-75 flask. The culture medium consisted of McCoy's 5A medium with HEPES ("N-2-hydroxyethyl-1-piperazine-N'-2-ethane sulfonic acid"), /12.5% fetal bovine serum ("FBS") /12.5% horse serum/1 uM hydrocortisone/1% penicillin/streptomycin. In 2–3 weeks, when monolayers had grown to confluency, two flasks of primary cultures derived from a given donor were trypsinized and passed into 6 flasks. After another 2–3 weeks, monolayer cultures were harvested for protein extraction as described below. Human leukemic cell lines, i.e., KG1a ("myeloid progenitor"), NALM-6 ("B-lymphoid progenitor"), JY ("B lymphoblastoid"), Ramos ("Burkitt's B-lymphoid"), HS-Sultan ("plasmacytoma") and K562 ("erythroleukemia") were maintained in RPMI 1640/9% FBS/1% penicillin/streptomycin. WIL-2 ("mature B-lymphoid") human leukemic cells were maintained in Iscove's medium/9% FBS/1% penicillin/streptomycin. T-lymphoblasts were derived by culturing peripheral blood mononuclear cells obtained from a normal adult donor in the presence of concanavalin A (2.5 ug/ml RPMI 1640/10% FBS/1% penicillin/streptomycin) for approximately 70 h (Dustin M. L., Springer T. A., *J. Cell Biol.* 107: 321 (1988), which is hereby incorporated by reference). Prior to their use as target cells, a sample of them was stained and verified microscopically for blast transformation. Remaining cells were washed ×2 in PBS(+) containing 5 mM α-methyl mannoside (Sigma) to neutralize any residual Con A and then ×2 in plain PBS(+) without α-methyl mannoside.

Example 13

Cell Lysis and Preparation of the Membrane Fraction

Tris-(hydroxymethyl)amino-methane and adenosine triphosphate ("ATP") were purchased from Sigma. PBS-CMF (PBS without calcium and magnesium) was obtained from GIBCO-BRL. An alkaline buffer consisting of 100 mM KCl/5 mM MgCl$_2$/1 mM ATP/ 25 mM Tris-HCl, pH 9.6 was used as the cell lysis buffer (Record M., Bes J-C, Chap H., Douste-Blazy L., *Biochem. Biophys. Acta* 688:57 (1982), which is hereby incorporated by reference). Medium from visibly confluent monolayer cultures (usually a batch of six T-75 flasks) was poured off; a 10 ml of cold PBS-CMF was added to each flask; the monolayers were scraped using a rubber policeman; and fragments were collected into a 50 ml centrifuge tube using a 10 ml pipet. Any remaining fragments were recovered by adding extra 10 ml of PBS-CMF.

Contents from 2 culture flasks were transferred to one 50 ml centrifuge tube and were washed by centrifugation for 10 min at 500 g (1500 rpm, Beckman TJ-6, TH-4 rotor). Supernatants were discarded and the pellets were suspended in approximately 2 ml of lysis buffer and pooled into one 15-ml centrifuge tube. An extra 6 ml of lysis buffer was added and washing by centrifugation was repeated. Finally, a cell pellet equivalent of 1 T-75 flask of stromal cells was resuspended in the 15 ml centrifuge tube in 1 ml of pre-chilled lysis buffer. It proved necessary to lyse cells in a Branson 250 sonifier (Branson Ultrasonics, Danbury, Conn.) as they could not be lysed by gentler methods, for example, suspending in a hypotonic buffer. To minimize generation of heat and prevent any foam during sonification, the sample tube was immersed in ice/salt/water bath at least up to the sample level. At a microtip setting of 6, two bursts of sonification, each of 10 sec duration, were applied with an interval of 1–2 min between them. The sonified contents were spun at 600 g in a refrigerated centrifuge at 4° C. for 10 min (Sorvall RT6000B; Du Pont, Wilmington, Del.). The 600 g pellet containing nuclear material and any unbroken cells was discarded. The supernatant (~6 ml) was distributed into three 12×75 mm polypropylene tubes (Sarstedt, Newton, N.C.) and centrifuged at a high speed (20,000 g) for 20 min at 4° C. in a Sorvall centrifuge (RC-5, Superspeed Refrigerated Centrifuge). The 20,000 g supernatants comprising the cytosol proteins were discarded and the pellets encompassing the membrane fraction were saved as P-20s.

Example 14

Electron Microscopy of P-20 Pellets

P-20 pellets were prepared as described above from monolayers of stromal cells which were harvested by mechanical scraping. They were fixed in 2.5% glutaraldehyde in Millonig's buffer for 3 h, washed with the same buffer for 2×15 min, and post-fixed in 1% osmium tetroxide for 30 min, dehydrated through graded alcohols, and propylene oxide, and embedded in Medcast resin. Ultrathin sections of pellets, stained with uranyl acetate and lead citrate, were examined in a Hitachi H-7100 electron microscope.

Example 15

Sequential Extraction of Membrane Proteins from P-20 Pellets

Tris, CHAPS ("3- [(3-cholamidopropyl)dimethylammonio]- 1 propanesulfonate"), EGTA ("ethylene glycol bis(β-aminoethylether) N,N-tetraacetic acid"), PMSF ("phenylmethylsulfonyl fluoride") and leupeptin were purchased from Sigma; 0.5M EDTA ("ethylenediaminetetraacetic acid") was from USB (Cleveland, Ohio); Triton® X-100 and ultrapure urea were from Bio-Rad (Hercules, Calif.); ultrapure LDS was from ICN (Schwarz/Mann Biotech, Cleveland, Ohio); glycerol was from Pharmacia LKB (Piscataway, N.J.); and DTT ("dithiothreitol") was from Fisher Biotech (Fisher Scientific, Fair Lawn, N.J.).

The P-20 membrane pellets (prepared from monolayers following mechanical scraping, involving no trypsinization) were sequentially solubilized in a series of three extraction buffers containing different detergents. The buffers consisted of (in sequential order): 2% (w/v) Triton® X-100 in PBS-CMF; 0.575% (w/v) lithium dodecyl sulfate ("LDS")/20% glycerol in 125 mM Tris-HCl, pH 6.8; and 8M urea/2% CHAPS/25 mM DTT in 50 mM Tris-HCl, pH 7.5. All three extraction buffers contained lmM EDTA, 1 mM EGTA, 1 mM PMSF and 10 ug leupeptin/ml as protease inhibitors. A P-20 pellet in a 12×75 mm polypropylene tube (Sarstedt) was dispersed in an extraction buffer (250 ul per pellet equivalent of 1 T-75 flask) by drawing through graded syringe needles (20G, 25G, and 27G, usually 3×with each needle) and gentle vortexing; the pellets were pooled into one 12×75 mm tube containing a mini stir bar; then the tube was placed in a beaker which in turn was placed on a magnetic stirrer for 1 h in the cold room, providing continuous gentle mixing. At the end of incubation, the contents were centrifuged at 20,000 g in a Sorvall centrifuge for 20 min at 4° C. The 20,000 g supernatant was aliquoted and saved as Triton® X-100 extract at −40° C. The remaining pellet was suspended in the next extraction buffer and the procedure was repeated. By the end of this protocol, the P-20 membrane pellets almost entirely solubilized. The protein extracts were aliquoted and stored frozen at −40° C. Protein extracts were fractionated by lithium dodecyl sulfate-polyacryl amide gel electrophoresis ("LDS-PAGE") as described below.

Sufficient membrane proteins are obtained by this technique using cells grown from a single donor to allow multiple cell binding assays to be performed. Starting with a bone marrow sample from a single donor, six T-75 flasks of first passage cultures of stromal cell monolayers were grown in about three to five weeks. They generate ~1.2 ml of LDS-solubilized membrane proteins (after accounting for losses), yielding ~20 aliquots of 60 ul each. Each aliquot after diluting 1:2 with Tris-HCl buffer, provides a sample of 120 µl for loading at least 3 lanes, each with 35 ul. Thus 20 aliquots, obtained from six flasks derived from a single donor, provide sufficient material to run at least 60 lanes and detect cell binding, demonstrating the feasibility of the present method. The technique has provided reproducible results using stromal cells derived from several different donors.

Example 16

LDS-PAGE, Electrophoretic Protein Blotting, Coomassie Blue Staining of Gels, and Coomassie Blue Staining of Protein Blots Bone marrow stromal cell membrane protein extracts, and rs-VCAM-1 were fractionated by LDS-PAGE using "native" 4–12% discontinuous gradient gels and electrophoretically transferred to PVDF. Necessary precautions were observed during electrophoresis and blotting to maintain cold conditions and avoid thermal denaturation of proteins.

On the other hand, the detergent-induced denaturation of proteins may have been reversed by removal of detergents from sample proteins during LDS-PAGE and subsequent blotting. Such a built-in mechanism of removal of detergents from sample proteins is thought to be one of the important reasons for preservation or restoration of cell adhesion function of membrane proteins by the present cell blotting system.

Protein gels and blots were stained by Coomassie Blue as described (Pharmacia LkB Instruction Manual: Excel Gel Precast Gels and Buffer Strips for Horizontal SDS Electrophoresis, Uppsala, Sweden, Pharmacia LkB Biotechnology (1989) and LeGendre, N., Matsudaira, P., Matsudaira PT (ed): *A Practical Guide to Protein and Peptide Purification for Microsequencing*, San Diego, Calif., Academic Press (1989) p. 57, respectively, which are hereby incorporated by reference).

Example 17

Western Blotting

Anti-VCAM-1 mouse monoclonal antibody ("MAb 4B9") was purchased from Genzyme (Cambridge, Mass.); anti-CD54 ("clone 84H10") and anti-CD44 ("clone J-173") were obtained from AMAC, Inc (Westbrook, Me.); and horseradish peroxidase-conjugated rabbit anti-mouse IgG was purchased from Cappel (Organon Teknika, Durham, N.C.). The protocol for blocking of nonspecific binding sites on PVDF was same as that used for cell adhesion assay on protein blots. Immunoperoxidase staining was performed using 3-amino-9-ethyl-carbozole (AEC) as substrate (Pluskal M. G., Przekop M. B., Kavonian M. R., Vecoli C., Hicks D. A., *Bio. Techniques* 4:272 (1986), which is hereby incorporated by reference).

Example 18

Cell Adhesion Assay on Protein Blots; Propidium Iodide Staining and Hematoxylin Staining of Cell Bands on PVDF Nonspecific binding sites on PVDF blots were blocked by incubating in 5% BSA/PBS(+) (phosphate-buffered saline containing calcium and magnesium purchased from GIBCO-BRL) for 1 h at room temperature, followed by overnight incubation in 1% BSA/PBS(+) in the cold room (4° C.). Cell adhesion was assayed both at 4° C. and 37° C. (i.e., in a standard tissue culture incubator) following the protocols described. Target cells were washed once in PBS-CMF by centrifugation. Cells were resuspended (at 1.5–3× $10^6$/ml) in 30 ml of 1% BSA/PBS(+) or 5% FBS/RPMI 1640, depending on whether the adhesion assay temperature is at 4° C. or 37° C., respectively. Notably, to avoid nonspecific adherence of cells to the background at 37° C., BSA was substituted for FBS in the cell incubation medium and washing media. Prior to adding cells, blots were washed 3×5 min using 0.5% BSA/PBS(+) or 5% FBS/PBS(+) and then cell incubations were carried out in appropriate adhesion assay chambers at 4° C. or 37° C. for 90 min or 60 min, respectively. Following cell incubation, blots at 4° C. were washed 3×5 min using cold 0.5% BSA/PBS(+); and blots at 37° C. were washed 3×5 min using 5% FBS/PBS(+) pre-warmed to 37° C. and incubating during washes in a 37° C. oven. Cell blots were fixed in 10% neutral buffered formalin for 2 hours at room temperature. Cell bands were developed by PI staining or hematoxylin staining (following the method of stain A followed by stain B). Cell bands stained by PI were viewed under long wave UV light. Adherent cells were visualized using fluorescence microscope equipped with epi-illumination and a UV excitation filter. Cell bands stained by hematoxylin were visualized using a standard transmission light microscope.

Example 19

Figure 10:
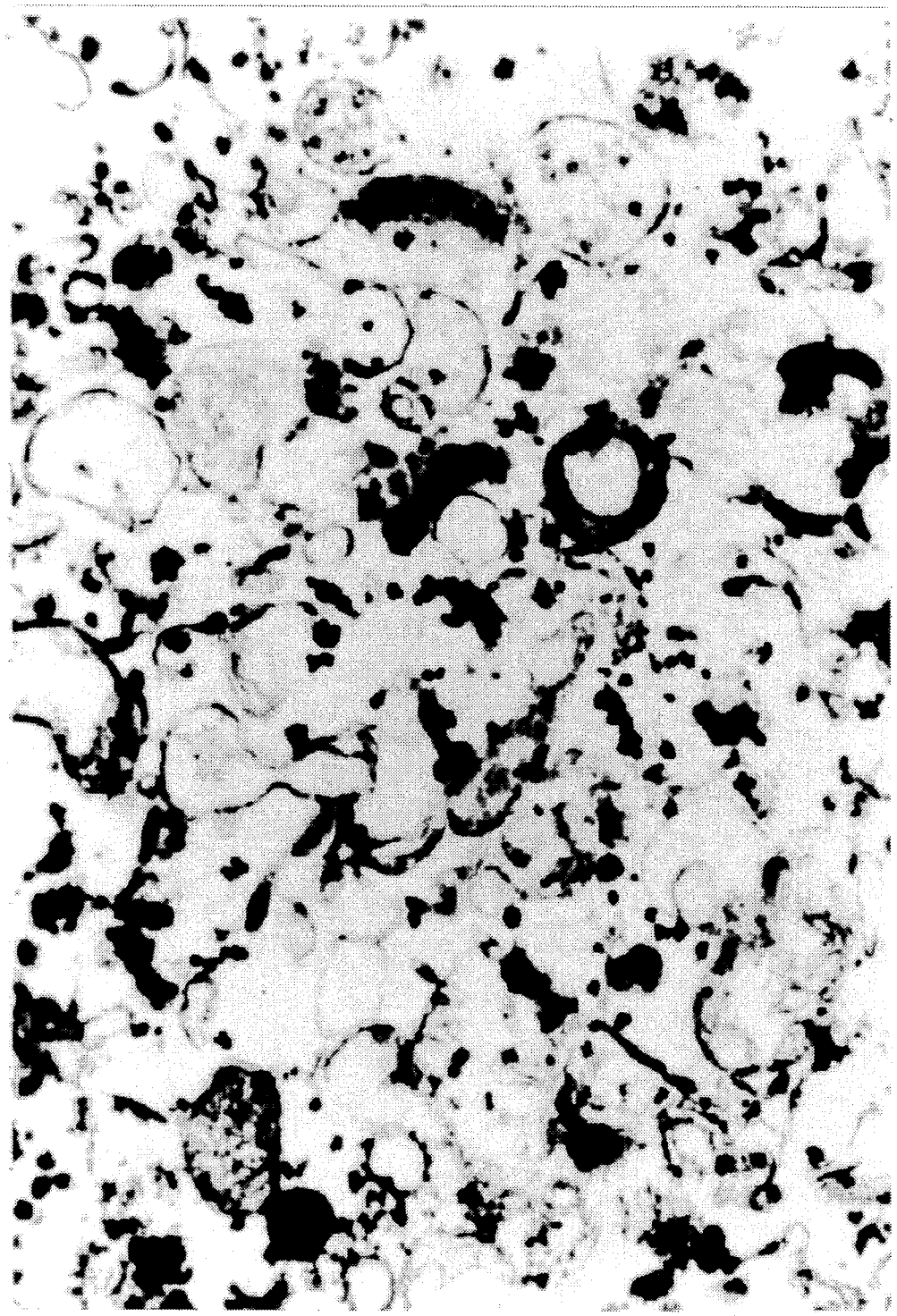
FIG. 10 is an electron micrograph of bone marrow stromal cell 20,000 g pellet (P-20) showing plasma membrane vesicles. Confluent monolayers of bone marrow stromal cells were harvested and a stromal cell membrane pellet (P-20) was prepared as described and submitted for standard electron microscopic study. What is shown here is a representative picture. Note that P-20 preparation is enriched for numerous vesicles consistent with plasma membranes. Occasional mitochondria, small dense particles morphologically consistent with glycogen particles, remnants of Golgi apparatus, scarce granular endoplasmic reticulum, lysosome-like dense bodies, and occasional lipid droplets consistent with adipocyte differentiation typical of stromal cells are also present in the sample (original magnification 45,000×).
Figure 11A:
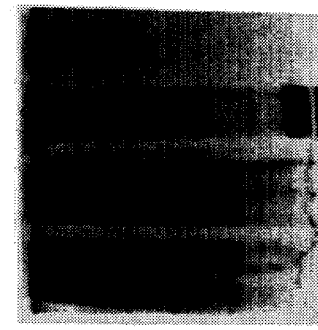
FIGS. 11A–D show cell adhesion to bone marrow stromal cell membrane proteins fractionated by lithium dodecyl sulfate-polyacryl amide gel electrophoresis using a 4–12% discontinuous gradient gel, and blotted onto a polyvinylidene difluoride membrane. Stromal cell membrane proteins were prepared as described. Samples are as follows: lane 1, membrane proteins extracted by 2% Triton® X-100 (lipid rich material floating at top of supernatant); lane 2, membrane proteins extracted as in lane 1 but representing the clear portion of supernatant; lane 3, membrane proteins extracted by 0.575% lithium dodecyl sulfate; and lane 4, membrane proteins extracted by 8M urea/25 mM dithiothreitol/2% (3-[3-cholamidopropyl)-dimethylammonio]-1 propanesulfonate). All final samples contained 0.2875% lithium dodecyl sulfate and 10% glycerol in 125 mM Tris-HCl, pH 6.8, and were loaded as 35 ul/lane.

Preparation, Electrophoretic Separation and Blotting of Stromal Cell Membrane Protein Extracts As the electron micrograph in FIG. 10 shows, the 20,000 g pellets (P-20s) representing BM stromal cell membrane fractions were enriched in plasma membrane vesicles. The P-20 preparations were sequentially solubilized by different detergents including Triton® X-100, LDS, and urea/DTT/CHAPS in sequential order until the pellet almost completely disappeared. The 20,000 g supernatants containing solubilized membrane proteins were fractionated by LDS-PAGE using 4–12% discontinuous gradient mini gels. As shown in FIG. 11A, excellent resolution of proteins was obtained. As judged by banding patterns, much more than half of the total amount of proteins seems to have been solubilized by Triton® X-100 prior to LDS extraction. This strategy significantly enriched proteins to be solubilized by LDS. Consequently, LDS extract showed fewer but more prominent protein bands. Urea/DTT/CHAPS solubilized any remaining proteins after Triton® X-100 and LDS extractions. Sufficient membrane proteins can be obtained by this technique using cells grown from a single donor to allow multiple cell adhesion assays to be performed. The results reported here have been reproduced using stromal cells derived from multiple different donors.

Figure 11B:
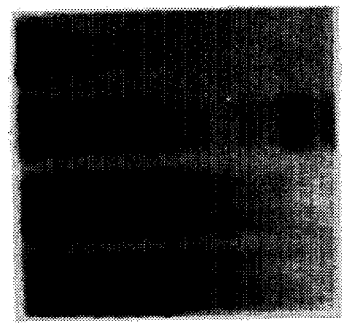

Proteins were transferred to PVDF electrophoretically. As shown in FIG. 11A and FIG. 11B, most bands seen on gel are represented on the blot as well. The transfer buffer consisted of standard Tris-glycine buffer (pH ~8.7) containing no LDS or sodium dodecyl sulfate ("SDS") or methanol. As can be expected and as judged by staining of gels following transfer, the transfer of certain proteins was not quantitative. For example, as shown in FIG. 13A and FIG. 13B, rs VCAM-1 transferred completely whereas wheat germ agglutinin transferred with difficulty.

Example 20

Cell Adhesion to Human BM Stromal Cell Membrane Protein Bands on PVDF

Figure 11C:
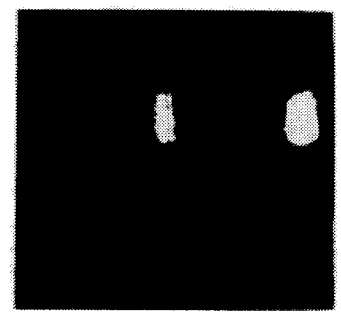
Figure 11D:
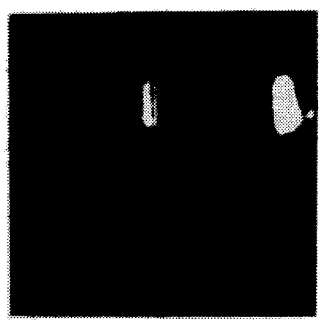
Figure 15A:
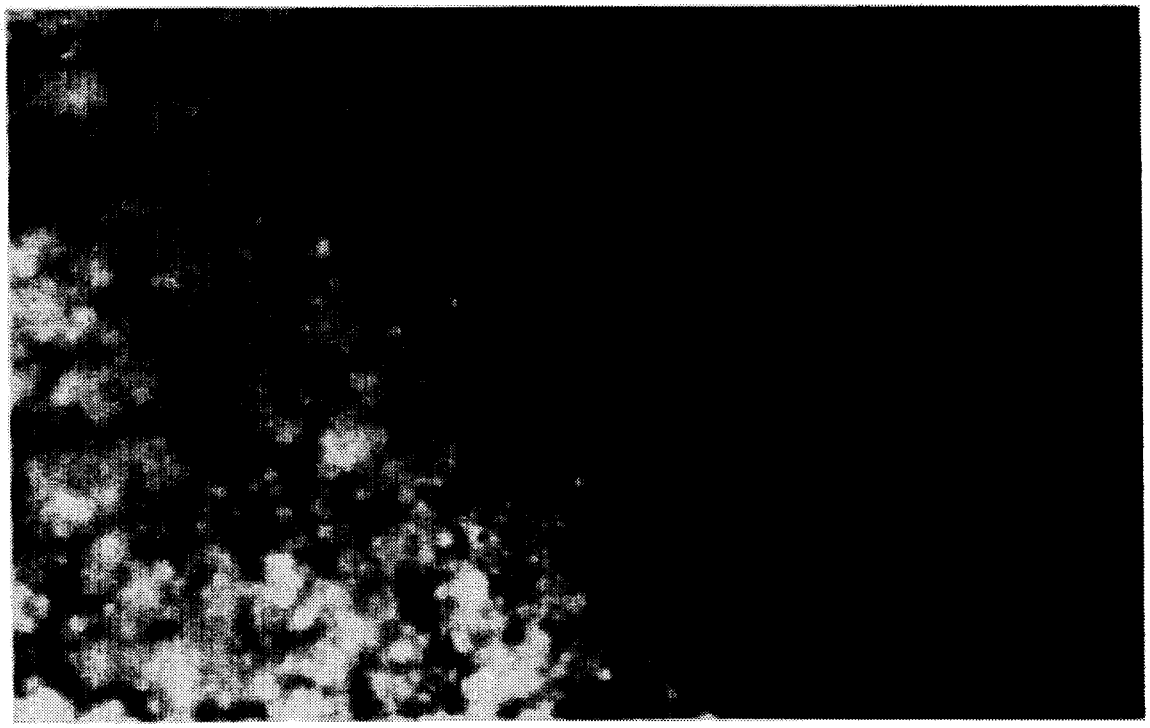
FIGS. 15A–B are photomicrographs of cells adherent to bone marrow stromal cell membrane protein bands on polyvinylidene difluoride membrane, stained by propidium iodide. Blots were viewed under a fluorescence microscope with epi-illumination and a UV excitation filter.
Figure 15B:
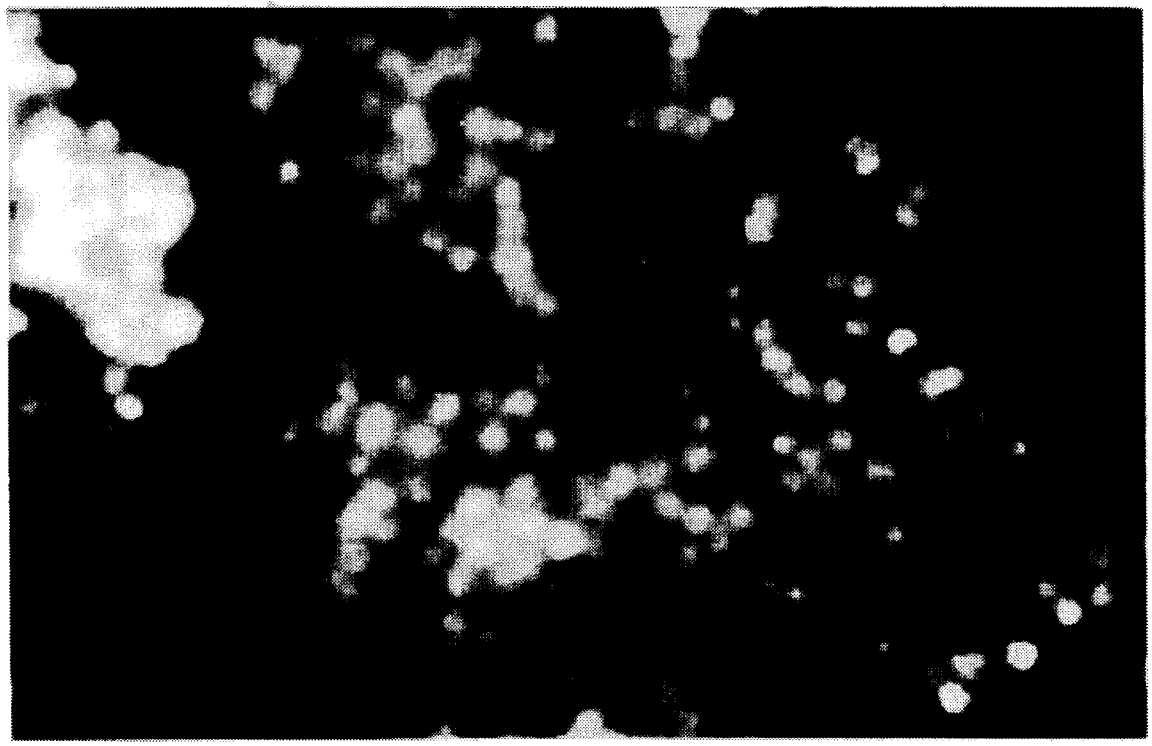
Figure 16A:
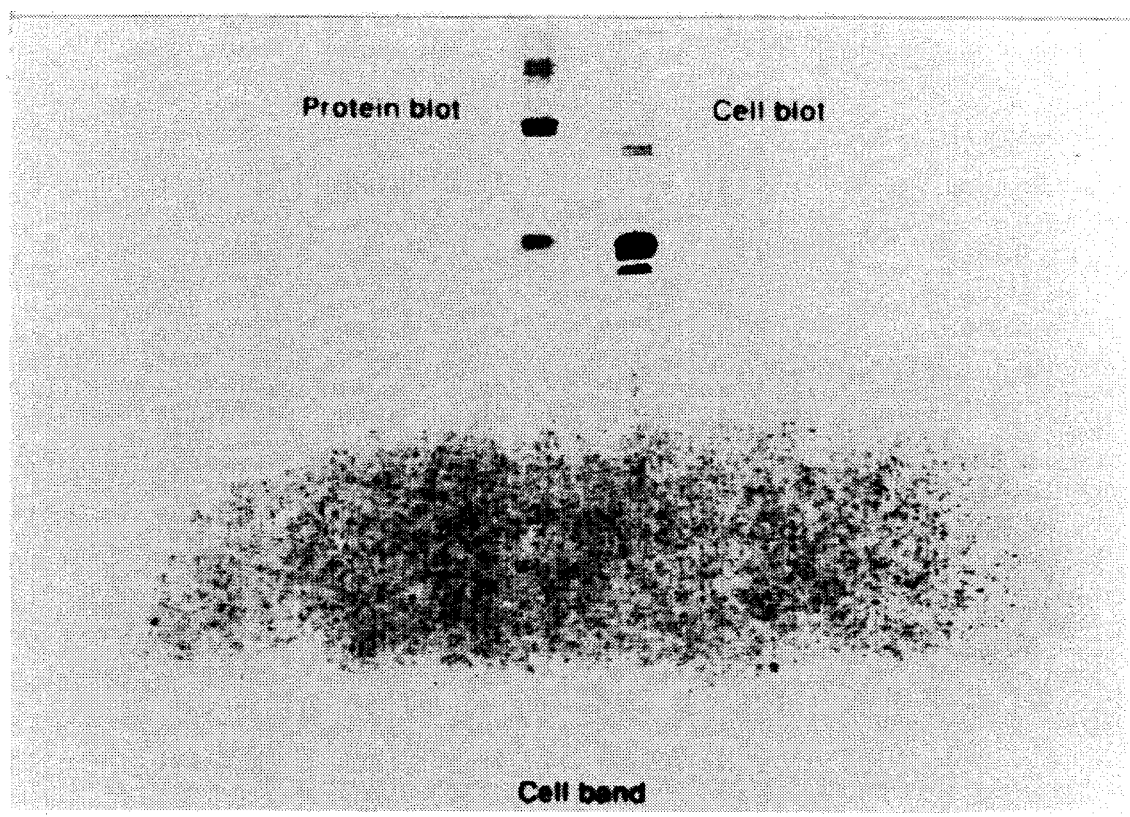
FIGS. 16A–B are photomicrographs of cells adherent to bone marrow stromal cell membrane protein bands on polyvinylidene difluoride membrane, stained by hematoxylin.
Figure 16B:
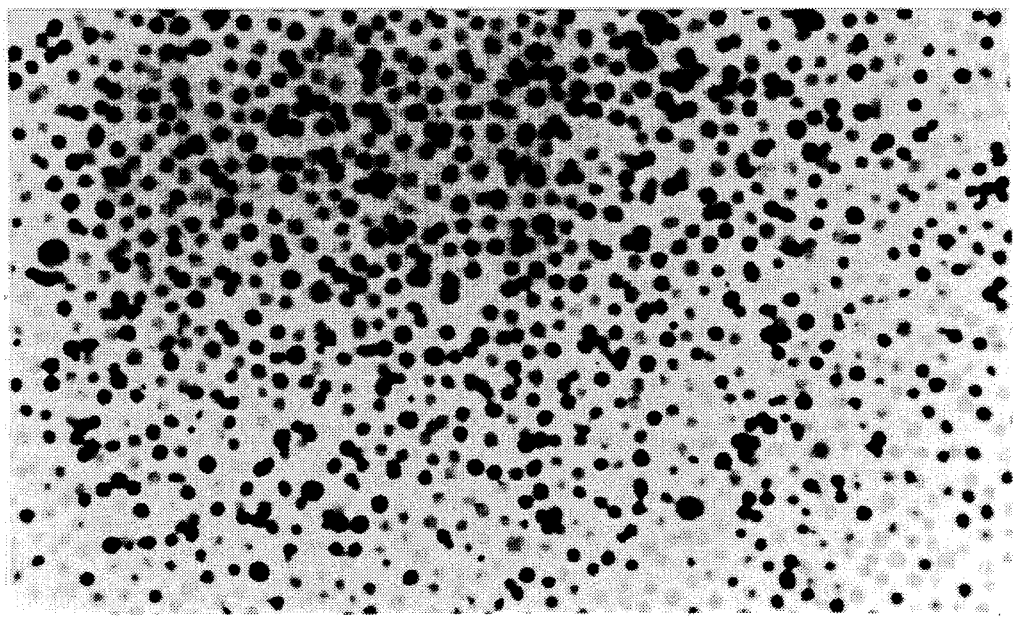

The LDS-extracted membrane protein sample revealed six bands by 4–12% gel showing lymphoid (NALM-6) cell adhesion (FIG. 11C, lane 3); apparently the same bands are also exhibiting adhesion to the progenitor myeloid (KG1a) cells (FIG. 11D, lane 3). The split bands are distinctive and indicate the specificity of the adhesion interactions in this new assay. The lack of adhesion of cells to the background of the blot and to additional multiple protein bands visible by Coomassie Blue staining further underscores the specificity of the cell binding observed. One protein band extracted by Triton® X-100 selectively binds the lymphoid (NALM-6) cells (FIG. 11C, lanes 1 and 2). The stromal cell proteins solubilized by urea/DTT/CHAPS (FIG. 11C, lane 4) show no cell adhesion. The negative results with urea/DTT/CHAPS-soluble fraction may be due to absence or denaturation of any adhesion molecules remaining in the membrane fraction after removal of proteins solubilized by Triton® X-100 and LDS. The cell adhesion assay temperature also showed a striking effect on cell binding to stromal cell membrane proteins. As shown above, assayed for cell binding at 4° C., KG1a cells showed adhesion to six stromal cell protein bands. In contrast, as shown in FIG. 14B, KG1a cells at 37° C. adhered to nine distinct stromal cell protein bands. The BM CAMs exhibiting cell adhesion at 4° C. are unlikely to be integrins since cell adhesion involving integrins is mostly observed at 37° C. (Makgoba M. W., Sanders M. E., Shaw S., *Immunoloqy Today* 10:417 (1989); Seth R., Salcedo R., Patarroyo M., Makgoba M. W., *FEBS Letters* 282: 193 (1991), which are hereby incorporated by reference). Positive bands were confirmed as due to cell binding by microscopic visualization (FIG. 15 and FIG. 16).

As judged by molecular weight markers (FIG. 13A), some of the BM CAMs detected by cell blotting would appear to be of extremely LMW ("low molecular weight") proteins, approaching as low as 10–15 KDa. LDS has a great affinity for polyacrylamide in the cold conditions leading to deficiency of LDS in the frontal region of the gel and accelerated migration of LMW proteins. Therefore, it is important to bear in mind that the positions of protein bands in the LDS-PAGE gel do not necessarily correspond to the true molecular weights, and may grossly underestimate the molecular weights.

It is also of interest to note that when LDS extracts were fractionated by 4–20% continuous gradient gel (instead of 4–12% discontinuous gradient gel), the two HMW ("high molecular weight") protein bands (shown in FIG. 11C and FIG. 11D, lane 3) lost their cell adhesive function. As revealed by studies using various lectins, these gel systems are quite distinct. The 4–12% discontinuous gradient gel tended to favor or preserve multimeric complexes whereas 4–20% continuous gradient gel tended to dissociate and resolve them into monomeric units. Based on such observations, the HMW protein bands in LDS lane of 4–12% gel exhibiting NALM-6 and KG1a cell adhesion may represent functional complexes of polypeptides that became dissociated in the 4–20% gel and lost their adhesive function. Similarly, the LMW proteins in LDS lane of 4–12% gel may represent different monomeric proteins which retain their adhesive function even after separation by 4–20% gel electrophoresis.

BM is distinctive among all organs for the multiplicity of cell types and myriad cell to cell interactions. It is viewed as the "breeding ground" for all blood cell types, except perhaps for T lymphocytes. Therefore, adhesion of different hematopoietic cell types was investigated using this system to identify possible lineage-specific adhesion proteins. The cell types that have been studied included, in addition to KG1a ("progenitor myeloid") and NALM-6 ("progenitor B-lymphoid"), JY ("B lymphoblastoid"), Ramos ("Burkitt's B-lymphoid"), WIL-2 ("mature B-lymphoid"), HS-Sultan ("plasmacytoma"), K562 ("erythroleukemia") human leukemic cell lines, and Con A-induced T-lymphoblasts. As shown in FIG. 5, different hematopoietic cells exhibit adhesion to different subsets of BM CAMs notwithstanding most of the cells exhibit adhesion to some common BM CAMs. T-lymphoblasts, as can be expected, showed minimal or no binding to any BM CAMs further underscoring the specificity of cell adhesion mediated by these proteins. It is also intriguing that progenitor cells (i.e., KG1a and NALM-6) bound to greater number of stromal cell protein bands than more mature cell types (i.e., WIL-2 and JY B lymphoblastoid cells) did. These findings provide a new avenue to study of molecular mechanisms for determining specificity to hematopoietic cellular localization within BM microenvironment and of hematopoiesis.

Example 21

Western Blotting

Figure 12A:
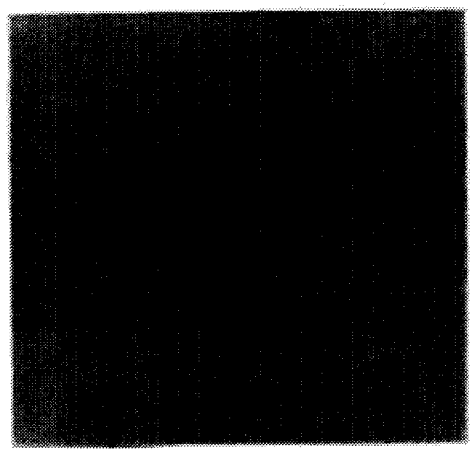
FIGS. 12A–C shows the western blotting analysis of bone marrow stromal cell membrane proteins using antibodies to known cell adhesion molecules.
Figure 12B:
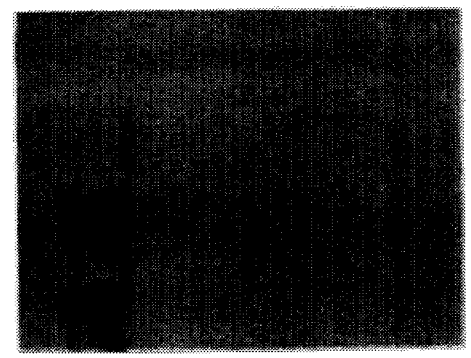
Figure 12C:
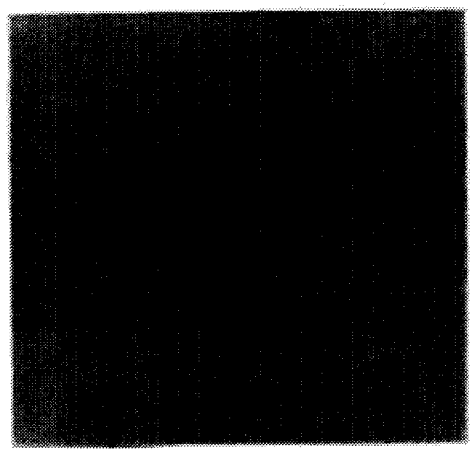

Western blotting of stromal cell membrane protein extracts using monoclonal antibodies to VCAM-1, CD54 and CD44 have identified all three molecules in the Triton® X-100 extracts (FIGS. 12A, 12B, 12C) but not the LDS extract. This is consistent with the observation that these molecules can be immunoprecipitated from Triton® X-100 lysates of stromal cells (Simmons P. J., Masinovsky B., Longenecker B. M., Berenson R., Torok-Storb B., Gallatin W. M., *Blood* 80: 388 (1992), which is hereby incorporated by reference). The electrophoretic mobilities of the known CAMs are remarkably different from those of the BM CAMs reported here pointing to novelty of the BM CAMs.

VCAM-1, CD54 and CD44, although identified by western blotting in Triton® extracts, did not exhibit cell binding, possibly because they may have been denatured by the system or are present below the sensitivity level of the present assay. To demonstrate the ability of this cell blotting system to preserve adhesion function of a known cell membrane adhesion protein, recombinant soluble VCAM-1 (rs VCAM-1) was tested.

Example 22

Cell Adhesion to Purified Protein of VCAM-1 rs VCAM-1 (Osborn L., Hession C., Tizard R., Vassallo C., Luhowskyj S., Chi-Russo G., Lobb R., *Cell* 59: 1203 (1989); Lobb R., Chi-Rosso G., Leone D., Rosa M., Newman B., Luhowskyj S., Osborn L., Schiffer S., Benjamin C., Douglas I., Hession C., Chow P., *Biochemical Biophysical Res Communications* 178: 1498 (1991), which are hereby incorporated by reference) was electrophoresed by LDS-PAGE and electroblotted along with BM stromal cell membrane protein extracts. As shown in FIG. 13 and judged by electrophoretic mobilities, the BM CAMs are quite distinct from VCAM-1. The cell adhesion assay at 37° C. showed binding of Burkitt's lymphoma (Ramos) cells to VCAM-1 band (FIG. 13C), as can be expected from earlier studies (Osborn L., Hession C., Tizard R., Vassallo C., Luhowskyj S., Chi-Russo G., Lobb R., *Cell* 59:1203 (1989), which is hereby incorporated by reference). This suggests that the present system, comprising of LDS-PAGE, electroblotting, and other steps, does retain the cell adhesion function of VCAM-1. The sensitivity of the assay approached as low as 0.3 ug of VCAM-1 loaded in a lane showing discernible cell band. It is concluded that VCAM-1, CD54 and CD44 are present below the sensitivity level of the assay since all known adhesion proteins that have been tested have retained their cell adhesion function by the present system. It should be remembered that the stromal cells that were used in the present study represented uninduced stroma. However, uninduced stroma expresses low levels of VCAM-1 (Simmons P. J., Masinovsky B., Longenecker B. M., Berenson R., Torok-Storb B., Gallatin W. M., *Blood* 80:388 (1992), which is hereby incorporated by reference). To detect these molecules in stromal cell extracts by cell blotting, it may be necessary to treat stroma with various cytokines prior to harvesting.

The BM proteins showing cell adhesion are novel CAMs for four major reasons: 1) Known CAMs, specifically VCAM-1, CD54, and CD44, have been identified by western blotting in Triton® extracts, obtained prior to LDS extraction, but not in LDS extracts; 2) The BM CAMs could be extracted only by LDS, whereas most known CAMs are solubilized by Triton® or NP-40 as well; 3) The electrophoretic mobilities of the novel BM CAMs, as detected by cell blot, are markedly different from those of known CAMs, as detectable by western blot (VCAM-1, CD54, CD44) and by simultaneously running purified material of one of them (rs VCAM-1) in a parallel lane; 4) Finally, four of the nine BM CAMs show cell adhesion not only at 37° C. but also equally well at 4° C., unlike cell adhesion involving integrins (for example, the interactions between LFA-1 (lymphocyte function-associated antigen-1 or CD11a) and CD54; and LFA-1 and ICAM-2)) which are temperature-dependent and are observed only at 37° C. (Makgoba M. W., Sanders M. E., Shaw S., Immunology Today 10:417 (1989); Seth R., Salcedo R., Patarroyo M., Makgoba M. W., *FEBS Letters* 282: 193 (1991), which are hereby incorporated by reference). Since the BM CAMs could only be solubilized by LDS, they would escape detection by conventional techniques, i.e., immunoprecipatation of proteins solubilized by Triton® or NP-40. Thus, cell blotting not only provides a direct approach for identifying CAMs but may also be capable of identifying CAMs not detectable by other techniques.

Although the invention has been described in detail for the purpose of illustration, it is understood that such details are solely for that purpose, and variations can be made therein by those skilled in the art without departing from the spirit and scope of the invention which is defined by the following claims.

What is claimed:

1. A method for detecting binding between cell adhesion molecule proteins and cells having a potential to be bound to such proteins comprising:

solubilizing a solid membrane pellet containing cell adhesion molecule proteins with lithium dodecyl sulfate to form a solution;

subjecting the solution to polyacrylamide gel electrophoresis to separate the cell adhesion molecule proteins by size and charge within the gel;

contacting the gel with a blotting material to transfer separated cell adhesion molecule proteins to the blotting material;

applying cells having a potential to bind to the cell adhesion molecule proteins to the blotting material;

staining cells adhering to the blotting material after said applying cells to detect adhesion of the cell adhesion molecule proteins to the applied cells; and examining the stained cells adhering to the blotting material for indications of adhesion of the cell adhesion molecule proteins to the applied cells, wherein said subjecting and/or said contacting is effective to clear lithium dodecyl sulfate from the cell adhesion molecule proteins.

2. A method according to claim 1 further comprising:

growing cells bound to cell adhesion molecule proteins on the blotting material, prior to said staining.

3. A method according to claim 1 further comprising:

solubilizing the pellet, prior to said solubilizing in lithium dodecyl sulfate, in 2% nonaethylene glycol octylphenol ether solution to form a solution of cellular materials; and centrifuging the solution of cellular materials to form a further pellet, wherein the further pellet is subjected to said solubilizing in lithium dodecyl sulfate.

4. A method according to claim 1, wherein the blotting material is selected from the group consisting of polyvinylidene difluoride, nitrocellulose, and nylon membranes.

5. A method according to claim 1, wherein said staining is carried out with a stain selected from the group consisting of propidium iodide, hexatoxylin, and Wright/Giemsa stain, Papanicolau stain, and immunoperoxidase.

6. A method according to claim 1, further comprising:

providing a sample of cells;

lysing the cells to form a cell lysate;

separating cell nuclear materials from the cell lysate to form a residual fraction; and centrifuging the residual fraction to form the pellet to be solubilized in lithium dodecyl sulfate.

7. A method according to claim 1, wherein the cell adhesion molecule proteins have an unknown identity and the cells have a known identity.

8. A method according to claim 1, wherein the cell adhesion molecule proteins have a known identity and the cells have an unknown identity.

\* \* \* \* \*